US006677302B2

(12) United States Patent
Faller

(10) Patent No.: US 6,677,302 B2
(45) Date of Patent: Jan. 13, 2004

(54) COMPOSITIONS AND METHODS FOR THE TREATMENT OF VIRAL DISORDERS

(75) Inventor: Douglas V. Faller, Weston, MA (US)

(73) Assignee: The Trustees of Boston University, Boston, MA (US)

( * ) Notice: Subject to any disclaimer, the term of this patent is extended or adjusted under 35 U.S.C. 154(b) by 0 days.

(21) Appl. No.: 09/756,489

(22) Filed: Jan. 8, 2001

(65) Prior Publication Data

US 2001/0009922 A1 Jul. 26, 2001

Related U.S. Application Data

(63) Continuation of application No. 08/687,671, filed on Jul. 26, 1996, now Pat. No. 6,197,743.

(51) Int. Cl.$^7$ ...................... A61K 31/711; A61K 38/00
(52) U.S. Cl. ..................... 514/2; 424/184.1; 424/198.1; 424/278.1; 514/43; 514/44
(58) Field of Search ........................... 424/278.1, 184.1, 424/198.1; 514/2, 43, 44

(56) References Cited

U.S. PATENT DOCUMENTS

| | | | |
|---|---|---|---|
| 5,858,365 A | | 1/1999 | Faller |
| 6,197,743 B1 | * | 3/2001 | Faller .............................. 514/2 |

FOREIGN PATENT DOCUMENTS

| | | |
|---|---|---|
| EP | 0 069 659 | 1/1983 |
| EP | 0 324 574 | 7/1989 |
| EP | 0 546 261 | 6/1993 |
| EP | 0 546 261 A2 | 6/1993 |
| WO | WO 91/01719 | 2/1991 |
| WO | WO 93/07866 | 4/1993 |
| WO | WO 95/10271 | 4/1995 |
| WO | WO 95/11699 | 5/1995 |
| WO | WO 96/02244 | 2/1996 |
| WO | WO 96/27369 | 9/1996 |

OTHER PUBLICATIONS

Massimo Colombo, Natural history and pathogenesis of hepatitis C virus related hepatocellular carcinoma, Journal of Hepatology 1999; 31: Suppl. 1): 25–30.*
F. Abbott et al., *Neuropharmacology*, 27(3):BP287–294 (1988).
D. Faller et al., *Proceedings of the American ABQssoc. for Cancer Research*, Abstr. 2808, 37:411 (1996).
J. Watkins et al., *Research Commun. in Chem. Pathology and Pharmacology*, 39(3):355–364 (1983).
Antoni, et al., "NF–k B–Dependent and –Independent Pathways of HIV Activation in a Chronically Infected T Cell Line", *Virology*, 202:684–694 (1994).
Bohan et al., "Mutational Analysis of Sodium Butyrate Inducible Elements in the Human Immunodeficiency Virus Type 1 Long Terminal Repeat", *Virology*, 172:573–583 (1989).

Sadaie et al., "Induction of Developmentally Programmed Cell Death and Activation of HIV by Sodium Butyrate", *Virology*, 202:513–518 (1994).
Golub et al., "Induction of Dormant HIV–1 by Sodium Butyrate: Involvement of the TATA box in the Activation of the HIV–1 Promoter", *AIDS*, 5(6):663–668 (1991).
Tang et al., "Memory of Butyrate Induction by the Moloney Murine Sarcoma Virus Enhancer–Promoter Element", *Biochem and Biophys Res. Comm.*, 189(1):141–147 (1992).
Yeivin et al., "Sodium Butyrate Selectively Induces Transcription of Promoters Adjacent to the MoMSV Viral Enhancer", *Gene*, 116:159–164 (1992).
Bohan et al., "Sodium Butyrate Activates Human Immunodeficiency Virus Long Terminal Repeat—Directed Expression", *Biochem and Biophys. Res. Comm.*, 148(3):899–905 (1987).
Miller et al., "Antibodies to Butyrate–Inducible Antigens of Kaposi's Sarcoma–Associated Herpesvirus to Patient with HIV–1 Infection", *The New England J. of Med.*, 334(20):1292–1297 (1996).
Faller et al., "Arginine Butyrate–induced Susceptibility to Ganciclovir in Epstein–Barr Virus (EBV)–Associated Lymphomas", *Proceedings of the Am. Assoc. for Cancer Res.*, 37:411–412 (1996).
Faller et al., "Arginine Butyrate–Induced Susceptibility to Ganciclovir in an Epstein–Barr Virus (EBV) Associated Lymphona", *Am. Soc. of Hematology [Blood]*, 86(10)(1):342a (1995).
Zhang, Z–X et al., *J. General Virology*, 65L37–46 (1984).
Bouregeade, M.F. et al., *Int'l J. of Cancer*, 24:314–318 (1997).
Huber et al., *Cancer Research*, 53:4619–4626 (1993).
Huber et al., *PNAS*, 91:8302–8306 (1994).
Vile et al., *Cancer Research*, 54:6228–6232 (1994).
Caruso et al., *PNAS*, 90:7024–7028 (1993).
DiMaio et al., *Surgery*, 116(2):205–213 (1994).
O'Malley et al., *Cancer Research*, 55:1080–1085 (1995).
Oldfield et al., *Human Gene Therapy*, 4:39–69 (1993).
Pouillart et al., *Int. J. Cancer*, 51:596–601 (1992).

(List continued on next page.)

*Primary Examiner*—David Guzo
(74) *Attorney, Agent, or Firm*—Nixon Peabody LLP

(57) ABSTRACT

This invention relates to compositions and methods for the treatment of virus infections and other viral-associated disorders. Compositions comprise an inducing agent and an anti-viral agent. The inducing agent induces the expression of a cellular or viral product, such as viral thymidine kinase, increasing the sensitivity of proliferating cells to the anti-viral agent. Typical anti-viral agents are nucleoside analogs such as ganciclovir that inhibit viral replication. Methods involve administration of therapeutically effective amounts of the inducing agent with the anti-viral agent to destroy virus-infected cells. Viral infections that can be treated include infections by herpes viruses such as Kaposi's-associated herpes virus and Epstein-Barr virus, HIV infections and HTLV infections. These compositions and methods are particularly effective against episomal and latent infections in proliferating cells.

14 Claims, 16 Drawing Sheets

OTHER PUBLICATIONS

Hurford et al., *Nature Genetics*, 10:430–435 (1995).
Lokeshwar et al., *Anticancer Research*, 15:93–98 (1995).

Donaldson et al., *Int. J. Cancer*, 57:847–855 (1994).

* cited by examiner

COMPOSITIONS AND METHODS FOR THE TREATMENT OF VIRAL DISORDERS

This application is a continuation of copending application Ser. No. 08/687,671, filed Jul. 26, 1996, now U.S. Pat. No. 6,197,743, which is hereby incorporated by reference.

BACKGROUND OF THE INVENTION

1. Field of the Invention

This invention relates to compositions and methods for the treatment of viral disorders. Treatment involves administration of an inducing agent, to induce expression of a product in a virus-infected cell, and an anti-viral agent, that acts on the expressed product to destroy the virus-infected cell.

2. Description of the Background

A growing number of cellular disorders such as neoplastic malignancies have been found to contain viral genetic sequences or virus particles in the anomalous cells. For a large number of these disorders, the presence of the virus is believed to be causative or at least contributory instrument. Representative members of many of the known families of viruses have been found in such cells including members of the herpes family of viruses, the polyomaviruses and the hepatitis viruses.

Epstein-Barr virus (EBV), a 172 kb herpes virus, is often found intimately associated with both mature and immature B cells and is believed to be involved to some degree in infectious mononucleosis, African Burkitt's lymphoma (BL) and nasopharyngeal carcinoma. EBV undergoes lytic replication after initial infection of oropharyngeal epithelia. The linear form genome is duplicated, packaged into the viral capsid and extruded from the cell by budding or lysis. One hundred viral proteins are synthesized during this lytic stage of the virus life cycle. In contrast, normal B cells incubated with EBV in vitro are efficiently immortalized and develop into continuously growing lymphoblastoid cell lines (LCLs). The cellular events that regulate these distinct outcomes are as yet unclear.

In immortalized cells, the genome circularizes, amplifies and replicates coordinate with, and dependent upon, cell division. Because no viral particles are produced, infection is considered to be latent and EBV persists in the cells for life. Outgrowth of latently infected B cells is prevented by T cell immune surveillance. In immortalizing latent infection, only 11 gene products are detected, including 6 nuclear antigens (EBNA-1, -2, -LP, -3A, -3B, -3Q), 3 membrane proteins (LMP-1, LMP-2A, LMP-2B) and two small, non-poly(A) RNAs (EBER-1 and EBER-2) (G. Miller et al., *Epstein-Barr Virus: Biology, Pathogenesis and Medical Aspects*, Raven Press, N.Y. 1990). In EBV(+) tumors such as Burkitt's lymphoma, neoplastic genetic events have often superseded the requirement for viral immortalizing functions, and gene expression may be limited to EBNA-1 (M. Rowe et al., EMBO J. 6:2743–51, 1987). Virus tropism is determined by complement receptor type 2 which mediates attachment of the envelope protein gp350/2204 to B and some T lymphocytes, follicular dendritic cells and epithelial cells.

EBV is a common and worldwide pathogen. Childhood infection is asymptomatic. About 50% of individuals with delayed exposure develop a self-limited, lymphoproliferative syndrome referred to as infectious mononucleosis. EBV is also detected in 2 endemic tumors, African Burkitt's lymphoma (BL) (G. Henle et al., Proc. Natl. Acad. Sci. USA 58:94–101, 1985) and nasopharyngeal carcinoma (NPC) (W. Henle et al., Adv. Viral Onco. 5:201–38, 1985), as well as gastric carcinoma, breast cancers and sarcomas. Recently, some T-cell and B-cell lymphomas, as well as about 50% of Hodgkin's lymphomas have been found to contain EBV (L.M. Weiss et al., N. Engl. J. Med. 320:502, 1989).

Burkitt's Lymphoma occurs in the United States at a prevalence of about 60 plus EBV patients per year and can occur several years after the primary EBV infection in immunocompetent patients. Burkitt's lymphoma is a monoclonal lymphoma, as opposed to infectious mononucleosis, which is a polyclonal disease. The disease is distinctly different in Africa, where it is endemic where about 97% of the population is EBV-positive with 100 sero-positives per $10^6$ children. In the U.S., infection is sporadic with about 20% EBV-positives and somewhat rare with 1–2 per $10^6$ sero-positive children or about 300 cases per year.

African Burkitt's lymphoma is characterized by rapid growth of the tumor at non-lymphoid sites such as the jaw or the retroperitoneum. The tumor is of B cell origin and is closely related to the small noncleaved cells of normal lymphoid follicles. Biopsy specimens from African Burkitt's lymphoma invariably contain the EBV genome and are positive for EBNA (I. Magrath, *Epstein-Barr Virus and Associated Diseases*, pp. 631–43, M. Ninjhoff Publishing, Boston, 1986). This contrasts with the non-African Burkitt's lymphoma, in which only 15% to 20% of the tumors contain the EBV genome. EBV has a worldwide distribution and infects most (more than 90%) individuals before adulthood. The clustering of Burkitt's lymphoma in the equatorial belt of East Africa remains unexplained. It has been hypothesized that alterations of the immune system, possibly due to hyperstimulation by endemic malaria, may play an important role in the outcome of an EBV infection to individuals in this region (D. J. Moss et al., Int. J. Cancer 31:727–32, 1983). Individuals from this region show impairment in virus-specific cytotoxic T-cell activity. Normally, it is the T-cell response to EBV infection that limits B-cell proliferation, and this T-cell response is directly stimulated by EBV (H. zur Hausen et al., Nature 228:1056–58, 1970). It has been postulated that the failure of the T-cell immune response to control this proliferation could lead to excessive B-cell proliferation and, as such, provide a suitable background for further mutation, oncogenic transformation, and lymphomagenesis.

A scenario has been suggested for the involvement of EBV in the etiology of African Burkitt's lymphoma (G. Klein, Proc. Natl. Acad. Sci. USA 76:2442–46, 1979). The first step involves the EBV-induced immortalization of B lymphocytes in a primary infection. The second step involves the stimulated proliferation of EBV(+) B cells. This step is facilitated in the geographic areas where Burkitt's lymphoma is endemic (presumably because of the presence of malaria), through B-cell triggering and the suppression of T-cells involved in the control of the proliferation of EBV-infected cells. This pool of cells becomes increased in size as a target cell population for random chromosomal rearrangements. The third and final step is the reciprocal translocation involving a chromosomal locus with an immunoglobulin gene and the c-myc gene on chromosome 8. This leads to the deregulation of the c-myc gene, to the development of the malignant clone and to the appearance of a tumor mass (G. Klein et al., Nature 315:190, 1985). Alternative scenarios have been proposed in which the order of the steps are rearranged such that the B-cell activation by malaria precedes the chromosomal translocation and is followed by EBV infection. Regardless, the components of these two scenarios each account for the geographic distribution of Burkitt's lymphoma, the critical involvement of EBV in lymphomagenesis, and the eventual selection and clonal outgrowth of a population of cells with the critical translocation involving the deregulation of the c-myc gene on chromosome 8.

Treatment of Burkitt's lymphoma is most commonly chemotherapy, with radiotherapy playing a minor role. With this regiment, prolonged survival rates of 50% can be achieved.

Hodgkin's disease has an incidence in United States of about 3,500 EBV(+) patients per year. For more than 20 years, a role for EBV in the pathogenesis of Hodgkin's disease (HD) was postulated based on epidemiologic evidence linking Hodgkin's patients with EBV seropositivity and elevated EBV titers (A. S. Evans et al., Int. J. Cancer 34:149, 1984). A number of studies have found an increase (2–5 fold) in the incidence of HD after infectious mononucleosis. However, some Hodgkin's patients were seronegative for EBV and the association between EBV and Hodgkin's disease remained speculative until 1987. In that year, molecular genetic analysis demonstrated that some Hodgkin's tissues contained monoclonal EBV DNA and that the virus was localized to Reed-Sternberg (RS) cells (the malignant cells in HD). Subsequent immunohistochemical and serologic data support an association between EBV and Hodgkin's disease and confirm the localization of the virus to cytologically malignant-appearing RS cells and variants (N. M. Jiwa et al., Histopathology 21:51, 1992). EBV also infects variable numbers of small B and T lymphocytes in the reactive inflammatory cell infiltrate that composes the bulk of Hodgkin's tissues (L.M. Weiss et al., Am. J. Path. 139:1259, 1991).

In most series of cases reported to date, EBV is associated with approximately half of mixed cellularity Hodgkin's disease cases and a somewhat lower percentage of the nodular sclerosing subtype. In contrast, lymphocyte-predominant Hodgkin's disease is rarely EBV-associated. Although EBV DNA has been identified in the lymphocyte depletion variant of Hodgkin's disease, there is controversy over the morphologic criteria for diagnosis of this variant and its distinction from anaplastic large-cell lymphoma, in which EBV is also implicated as a pathogen Clonal and non-clonal EBV genomes are present in Hodgkin's disease. Expression of the oncogene LMP (latent membrane protein) is seen in RS cells. In HD, the region of the (viral) BNLFI oncogene coding for the amino terminal and transmembrane domains (associated with oncogenic function) of LW appears to be homogeneous, whereas the region coding for the intracytoplasmic (carboxyl terminal) domain of LMP is heterogeneous. Cytological similarities between RS cells and immunoblasts of known EBV-induced infectious mononucleosis and EBV induced AIDS-related lymphomas are consistent with the hypothesis that the EBV-BNLFI, oncogene is an inducer of morphological features of RS cells. Whether chromosomal integration of EBV DNA is an important factor in activation of such a transforming activity remains to be elucidated. Therefore the RS cells appear to be derived from lymphocytes beyond the pre-B-cell or common thymocyte stage, which may or may not subsequently become infected by EBV.

The high prevalence of EBV in Hodgkin's disease implies an etiologic role for the virus in Hodgkin's tumorigenesis. This pathogenetic theory is supported by the monoclonality of EBV DNA in these tumors (M. L. Gulley et al., Blood 83:1595–602, 1994). In one series, monoclonal EBV DNA was detected in all 17 cases having EBNA1-positive RS cells. Because tumor-associated viral DNA is monoclonal, it is likely that virus infection preceded clonal expansion. This reinforces the hypothesis that the virus is not an innocent bystander, but rather plays a role in the pathogenesis of the Hodgkin's disease and the other tumor types in which it is found (A. Neri et al., Blood 77:1092, 1991). The observation of EBNA1 expression in the RS cells of clonally-infected cases indicates that the clonal virus is localized to these cells and suggests that Hodgkin's disease results from the transformation of an EBV-competent cell. Other studies suggest that this virus is modulating rather than an etiologic agent in a considerable proportion of HD cases.

Investigations into the biology of EBV infection have shown that only one viral particle successfully infects a given cell. Once the viral DNA is established inside the cell, it circularizes and reproduces itself to yield multiple identical copies of viral DNA (E. A. Hurley et al., J. Exp. Med. 168:2059, 1988). In this way, tumors derived from infected cells can have multiple copies of EBV per cell, while maintaining clonal viral DNA structure. The average amount of clonal EBV DNA in Hodgkin's disease tissues varied from 0.5 to 5 copies per cell. Because RS cells comprised only a small fraction (<1%) of all HD tissue cells, the content of EBV DNA in each RS cell is estimated to be at least 100 times higher than the measured average copy number per cell, or at least 50 copies of viral DNA per RS cell. This is comparable with, or greater than, the viral burden in infected non-Hodgkin's lymphomas. The high copy number of EBV in RS cells may relate to the pathobiology of this complex lymphomatous disorder. In agreement with these studies, EBV DNA is abundant and monoclonal in infected RS cells. The presence of EBV in RS cells was strongly and independently linked to mixed cellularity histology and Hispanic ethnicity.

T-Cell non-Hodgkin's lymphoma (NHL) has a U.S. incidence of about 3,100 T-cell, EBV(+) NHL patients per year. Clonally-integrated EBV is found in association with T-cell lymphomas as well as B-cell lymphomas. Currently, three populations of tissue-restricted T lymphocytes have been recognized, mucosa-associated, cutaneous and nodal T lymphocytes. T-cell lymphomas arising from different sites, but with similar morphology may show differences in lymphomagenesis and in expression of oncogenies, adhesion molecules, presence of certain DNA/RNA viral sequences and in clinical presentation and behavior.

Primary cutaneous CD30(+) large cell, T-cell lymphomas often remain localized to the skin for a long time, express a unique cutaneous lymphocyte antigen (CLA), known as the skin-homing receptor, have been postulated to be associated with the presence of human T-cell leukemia/lymphoma virus type I (HTLV 1), and have a good clinical course (R. C. Beljaards et al., Cancer 71:2097, 1993). In contrast, morphologically similar T-cell lymphomas of nodal origin often behave more aggressively, are CLA-negative, and have been associated with the presence of EBV (P. C. de Bruin et al., Histopathology 23:127, 1993). There was no relation between primary cutaneous T-cell lymphoma and EBV.

In agreement with this finding, EBV is not present in lymphomatoid papulosis, a premalignant cutaneous lymphoproliferative disorder (M. E. Kadin et al., J. Pathol. 170:145, 1994). EBV-associated T-cell lymphomas are highly site-restricted and are morphologically indistinguishable from EBV(−) T-cell lymphomas (P.C. de Bruin et al., Blood 83:1612, 1994).

Nasal T-cell lymphomas are EBV-associated (F. C. S. Ho et al., Hematol. Oncol. 8:271, 1990). The frequency of EBV(+) primary pulmonary T-cell lymphoma is similar to the frequency of EBV(+) primary nodal T-cell lymphoma (J. Sabourin et al., Am. J. Surg. path. 17:995, 1993; P. C. de Bruin et al., Histopathology 23:509, 1993). EBV-associated primary gastrointestinal T-cell lymphomas seem to be rare, but recently a considerable number (36%) of enteropathy-associated T cell lymphoma cases (EAT CL) were reported to be EBV(+) (L. Pan et al., Pathology 170:137, 1993), although other studies did not find such an association. Angiocentric immunoproliferative lesions (AILs) of nose (also known as lethal midline granuloma), lung (also known as lymphomatoid granulomatosis), and skin are frequently associated with EBV (L. J. Medeiros et al., Am. J. Surg. Pathol. 16:439, 1992). Although all AILs in the nose were EBV-positive, the relation between angiocentricity and EBV seems to be more complex. Primary cutaneous and gastrointestinal AILs are EBV(−), whereas primary pulmonary AILs can be EBV(+) or EBV(−). There is no clear relation between angiocentricity and EBV, and only primary site seems to be important in the relation between peripheral T-cell lymphoma and EBV. Thus, there are site-restricted differences in the occurrence of EBV-infected peripheral T-cell lymphomas.

Infection of T cells by EBV most likely occurs via CR2 or CR2-like receptors (C. D. Tsoukas et al., Immunol. Today 14:56, 1993). The close contact between T cells and the upper respiratory tract epithelium, known for its reservoir function for EBV, probably make T cells in this region more vulnerable for EBV infection. The finding that EBV can be found in almost all tumor cells in most cases of primary extra-nodal, and especially nasal, T-cell lymphoma, in contrast to primary nodal T-cell lymphoma, where the number of EBV-infected neoplastic cells varies greatly between the cases argues for an etiologic role for EBV in these cases. Moreover, these cases often express LMP-1, known for its transforming and oncogenic properties in vitro and are reported to be monoclonal for EBV (I. Su et al., Blood 77:799, 1991). Thus, there are site-restricted etiologic differences between morphologically identical T-cell lymphomas, of which EBV might be one of many factors.

EBV-induced lymphoproliferative disease or lymphoma has an immunodeficiency incidence in U.S. of about 10,000 B-cell, EBV(+) lymphoma patients per year. EBV is very commonly associated with lymphomas in patients with acquired or congenital immunodeficiencies. These lymphomas can be distinguished from the classical Burkitt's lymphomas in that the tumors may be polyclonal. Tumors also do not demonstrate the characteristic chromosomal abnormalities of Burkitt's lymphoma described earlier. The pathogenesis of these lymphomas involves a deficiency in the effector mechanisms needed to control EBV-transformed cells. The rototypic model for this disease has been the X-linked lymphoproliferative (XLP) syndrome (D. T. Purtilo et al., Am. J. Med. 73:49–56, 1982). Patients with XLP who develop acute infectious mononucleosis exhibit the usual atypical lymphocytosis and polyclonal elevation of serum immunoglobulins and increases in specific antibody to VCA and to EA. During these infections, patients with XLP fail to mount and sustain an anti-EBNA response after acute EBV infection. The unique vulnerability of males with XLP to EBV infection is most likely due to an inherited immune regulatory defect that results in the failure to govern the cytotoxic T cells and NK cells required to cope with EBV.

Patients with iatrogenic immunodeficiencies, such as organ transplant recipients, are also at an increased risk for lymphomas, and these lymphomas often contain EBV DNA and EBNA. Also, patients with AIDS are at a higher risk for developing polyclonal lymphomas associated with EBV.

EBV-induced lymphomas are associated with immunosuppression. EBV-associated lymphoproliferative disease (EBV-LPD) is characterized by actively proliferating EBV (+) B-cells, frequently without overt malignant change. These immunoblastic lymphoma-like lesions have been identified in a variety of transplant patients, in patients with congenital immunodeficiency, and in patients infected with HIV (J. I. Cohen, Medicine 70:137–60, 1991). These so called post-transplant lymphoproliferative disorders (PTLD) are observed after all transplants, including kidney, bone marrow, heart, liver and lung transplantation. This increased incidence of EBV-LPD in this setting is likely due to the aggressive immunosuppression required after these transplants.

Phenotypically, immunoblastomas resemble large cell lymphomas (LCLs) in vitro. They express EBNA1–EBNA6 and LMP. Obviously, these cells proliferate because the surveillance of the host has broken down, rather than owing to any cellular escape (G. Klein, Cell 77:791–93, 1994). These tumors share several common features, including rapid progression, clinical aggressiveness and a tendency to grow at extra-nodal sites (E. B. Papadopoulos et al., N. Engl. J. Med. 330:1185–91, 1994). These EBV(+) B lympbomas generally have an ominous prognosis, especially if monoclonal. In some cases, rapid immune reconstitution has led to spontaneous regression of the tumor. In most cases, however, this has not been possible or is ineffective. EBV-LPD has been particularly tragic in the transplant setting, causing the death of recently "cured" patients who would be unlikely to develop such disease as their natural immune reconstitution occurred over time. Empirically, nonclonal PTLD may regress with decreased immunosuppression (if that is clinically feasible), whereas regression is less predictable in polymorphic, monoclonal tumors. In contrast, monoclonal monomorphic tumors are frequently more aggressive and tend to progress despite immune modulation. Treatment with nucleoside antivirals alone, surgery, cytotoxic chemotherapy, α-interferon with immune globulin, or B-cell directed complement fixing monoclonal antibodies, has rarely been successful. Recently, autologous, T-cell transfusions were applied with some success in LPD after allo-BMT, but are unlikely to become a routine therapy and would be inappropriate in tumors of host origin.

EBV's association with PTLD is based on several clinical observations. Almost all patients with PTLD have serologic evidence of an EBV infection and the disease involves a proliferative disorder of B cells. The B cell lymphoproliferation can be either monoclonal or polyclonal. EBV-LPD is characterized by latent viral replication. The genome persists as a circular episome within the infected B-cells, and lytic replication is restricted (C. M. Rooney et al., XVIII Intl. Herpesvirus Workshop, abstract B3–37, Jul. 25–30, 1993). Additional evidence that EBV is associated with post-transplant lymphoproliferative disorders is the finding that patients without any prior exposure to EBV are at highest risk for developing the lymphoproliferative disorder. Patients who are serologically EBV(−) are at the highest risk when receiving an EBV(+) transplant. Supporting this observation is the finding that EBV-associated PTLD is more frequent in children receiving transplants than in adults. The incidence of EBV-associated PTLD is three-fold greater in some series of pediatric transplantation. An intriguing report suggested that the EBV is carried with the graft. In this case, a common donor gave rise to PTLD in two separate organ recipients. Both recipients demonstrated the same chromosomal translocation in their tumors.

Lung transplant recipients are a special sub-group of patients at risk for developing PTLD. Most lung transplant recipients require relatively high immunosuppression for prevention of acute and chronic graft rejection. The development of PTLD and these patients has been estimated at 5% to 10%. Clinical presentation has ranged from systemic adenopathy to masses and infiltrates in the transplanted lung. The existing literature again indicates that there two distinct clinical syndromes in lung transplant recipients with PTLD. One scenario involves the polyclonal lymphoproliferative disorder commonly associated with mononucleosis and other benign lymphoproliferative diseases. This syndrome appears to respond to a decrease in the immunosuppressive regimen. The second clinical presentation involves a more aggressive form of lymphoproliferative disorder, one which histologically resembles immunoblastic non-Hodgkins lymphoma (NHL). This EBV-associated lymphoma is often monoclonal and can display an aggressive clinical course. For example, tumors are typically unresponsive to conventional chemotherapy and have been uniformly fatal. Although withdrawal of immunosuppression has been attempted in many cases, the recipients' dependency on graft function for adequate oxygenation complicates any reduction in the immunosuppression regimen.

The development of a large patient population with T-cell dysfunction in the 1980's, caused by profound iatrogenic immunosuppression required to facilitate solid organ and bone marrow transplantation. The AIDS epidemic led to the discovery of 2 additional EBV-related illnesses hairy leukoplakia (J. S. Greenspan et al., N. Engl. J. Med. 313:1564, 1985), and B-lymphoproliferative disease (EBV-LPD) (D. W. Hanto et al., Ann. Surg. 198:365–69, 1983).

As a result of effective antiretroviral therapy, prophylactic measures, and rigorous treatment of opportunistic infections (AIDS-related, EBV-associated lymphomas), HIV-infected individuals now live longer. More than 40% of people with AIDS will develop a neoplastic disease, resulting in severe morbidity and, often, death. Intermediate or high-grade B-cell lymphoma was added as an AIDS-related malignancy in 1985. Prolonged survival in HIV-infected patients is associated with increased incidence of lymphoma. Between 1940 and 1980, the VS incidence of lymphoma doubled. The AIDS epidemic, however, has superimposed on this underlying trend an additional risk of lymphoma between 60 and 100 times that expected in the HIV-negative population. Lymphoma, is likely to be a late manifestation of HIV infection, as documented in France where 33% of lymphomas occurred after an AIDS-defining illness. In the US, only about 3% of cases of AIDS are diagnosed simultaneously with lymphoma. Lymphoma occurs among all population groups at risk for HIV in all age groups and in diverse geographic regions. In the HIV-negative population, women have a lower incidence of lymphoma than men, and the incidence increases with age in homosexual/bisexual men and in hemophiliacs. The same incidence patterns are seen in the HIV-positive population, except among intravenous drug users, who may succumb relatively early to various infections.

Eighty to ninety percent of AIDS patients who are diagnosed with lymphomas are either intermediate or high-grade B-cell tumors, such as immunoblastic or large-cell types, or small noncleaved lymphoma, which may be subclassified as either Burkitt's or Burkitt-like. Among HIV-negative lymphoma patients, high-grade lymphomas represent only 10% to 15% of all lymphomas.

Etiology and pathogenesis of lymphomas in patients infected with HIV is multifactorial. Immunosuppression is thought to be a primary factor correlated with an increased incidence of lymphoma in several settings, including certain congenital immune deficiency diseases, autoimmune disorders, and the chronic use of immuno suppressive drugs, as occurs in patients who have undergone organ transplantation. Lymphomas which develop in these settings are similar to the AIDS lymphomas in terms of the pathologic type, the high frequency of extra-nodal disease at presentation, and the relatively poor prognosis. It is clear that EBV plays a major role in AIDS lymphomagenesis. This may perhaps be the result of damaged immunosurveillance of EBV-infected cells in AIDS patients.

There appears to be some biological significance to the site of disease. Patients with lymphoma primary to the central nervous system have an extremely poor prognosis and progressive HIV infection. About 75% have a history of AIDS as well as low CD4 cell counts (<50 mm$^3$) prior to development of lymphoma. Pathologically, these primary central nervous system lymphomas are almost always immunoblastic or large-cell lymphomas and uniformly associated with EBV. In contrast, improved prognosis has been associated with the large-cell type of systemic lymphoma, exclusive of the central nervous system. Clinicopathologic correlations are imprecise at best, because patients who develop lymphoma as the first AIDS-defining diagnosis may be distinct from those who develop lymphoma after preceding opportunistic illness.

SUMMARY OF THE INVENTION

The present invention overcomes the problems and disadvantages associated with current strategies and designs and provides novel compositions and methods for the treatment of viral and viral-associated disorders.

One embodiment of the invention is directed to pharmaceutical compositions that comprise an inducing agent to induce expression of a gene product in virus-infected cells and an anti-viral agent whose action is related to the activity of the gene product expressed. Inducing agents include cytokines or chemicals such as arginine butyrate or isobutyramide that induce the expression of the viral thymidine kinase gene in EBV-infected cells or other viral-specific enzymes. Effective anti-viral agents, such as substrates and substrate analogs such as nucleoside analogs, and inhibitors such as polymerase and transcriptase inhibitors, target cells that possess the induced activity for destruction.

Another embodiment of the invention is directed to methods for the treatment of viral disorders such as infections by treating infected mammals with a combination of an inducing agent and an anti-viral agent. The inducing agent induces a uniquely viral-process and the anti-viral agent targets induced cells for destruction. These methods are counter to conventional therapies that require either an antigenic viral expression, for elimination by the host immune system, or a suppression of viral activity in all forms. Disorders that can be successfully treated include mononucleosis, CMV retinitis and pulmonary disease.

Another embodiment of the invention is directed to methods for the treatment of cell-proliferative disorders resulting from viral infections. Treatment comprises administering a combination of an inducing agent and an anti-viral agent to infected mammals. The inducing agent induces a uniquely viral-process in the proliferating cells and the anti-viral agent specifically targets those cells for destruction. Disorders that can be successfully treated include viral-induced neoplasia such as certain B and T cell lymphoproliferative disorders, Burkitt's lymphoma, leukemias and other cell malignancies.

Another embodiment of the invention is directed to methods for the treatment of viral disorders including viral infections and virally-induced cell proliferative disorders. Treatment comprises administering a combination of an activator and an anti-viral agent to infected manmmals. Activators activate latent virus integrated into the infected or proliferating cells and the anti-viral agent specifically targets those cells for destruction. Disorders that can be successfully treated include latent infections such as infection by Kaposi's-associated human herpes virus, or human herpes virus type 8, human immunodeficiency virus and human T-cell leukemia/lymphoma virus.

Other embodiments and advantages of the invention are set forth in part in the description which follows, and in part, will be obvious from this description, or may be learned from the practice of the invention.

DESCRIPTION OF THE INVENTION

Figure 1A:
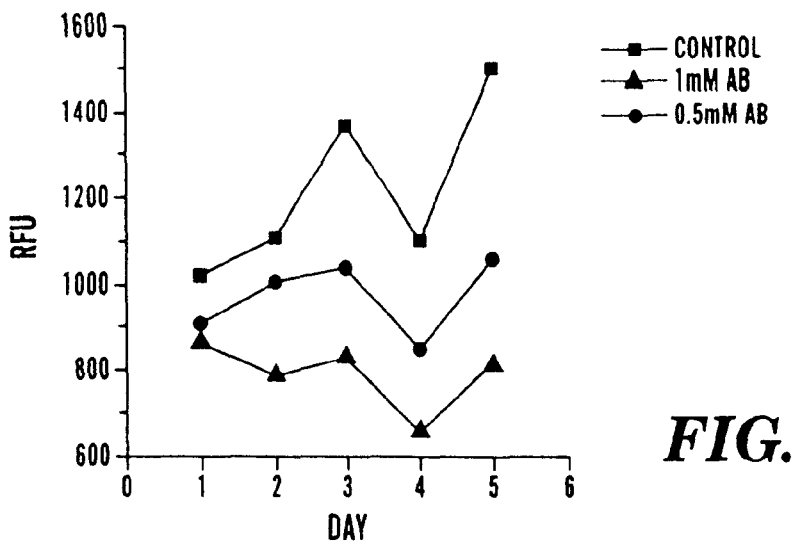
FIG. 1 Growth inhibition (a) of three human neuroblastoma cell lines, (b) SKNSH cells, and (c) the SY5Y cell line by arginine butyrate.

As embodied and broadly described herein, the present invention is directed to compositions and methods for the treatment of virus infections and other virus-associated disorders and, in particular, disorders associated with latent infections.

The traditional technique for treating a virus infection, whether active or latent, is to destroy the virus or the virus-infected cells with anti-viral agents. Anti-viral agents are chemical compounds or biological products that are lethal to the virus or the virus-infected cell. This technique is designed to eradicate diseased cells and thereby prevent further infections.

Treatments that destroy the infected cell typically target a basic cellular process such as replication or expression. These treatment regimens are most effective when targeting a specific enzyme such as a polymerase or reverse transcriptase. For example, inhibition of reverse transcription frustrates viral replication and prevents further propagation of the virus. Infected cells are killed by cell lysis or indirectly by the accumulation of viral products. As no infectious virus particles are produced, there are also no subsequent infections.

Unfortunately, anti-viral agents can have a detrimental effect on uninfected cells. Dosages required to destroy the virus-infected cells often effect related and even unrelated activities in otherwise normal cells. Tolerance and cellular accommodation to the single agent or drug is also quite common. Drug transport across the cellular membrane can increase, rendering the administered dose ineffective, and other cellular activities can compensate or substitute for the inhibited function. In addition, many infections are latent with no discernable manifestations. Symptoms can flare periodically over long periods of time. Treatment options are limited to continued amelioration of symptoms without any sort of real cure of the underlying infection. As a consequence, anticipated benefits of these agents are often unattainable or unrealized.

Viruses convert at least some portion of the molecular machinery of the infected cell to their own use. In doing so, the virus causes the cell to express viral or cellular products that allow the body to recognize that cell as infected. Infected cells, once recognized, can be targeted for elimination by the organism's own immune system. Problems arise when the immune system functions poorly or not at all and when the product is transiently expressed or rapidly mutates. These problems are typically associated with latent infections which are much more difficult to treat.

It has been discovered that viral infections can be effectively treated by taking advantage of a molecular process, preferably a necessary enzyme activity, that is uniquely viral (i.e. largely restricted to the virus or the virus-infected cell), and that can be acted upon by an anti-viral agent. The first step is not to inhibit that uniquely-viral process, as occurs with conventional therapy, but to actively promote that process. Virus-infected cells are than specifically targeted for destruction, not by the immune system, but by administration of the anti-viral agent whose ability to destroy infected cells relates to the viral activity that has been induced. This treatment combination has the surprising effect of forcing infected cells to become susceptible to selective killing. As a result, infected cells can be specifically targeted for elimination and previously untreatable infections arrested. Further, marginally or non-effective anti-viral agents can now be successfully administered because the therapeutically effective dose has been substantially reduced. The concentrations or frequencies of administration of effective compositions can also be reduced to lessen any harmful side-effects without reducing effectiveness against the virus-infected cells.

One embodiment of the invention is directed to a pharmaceutical composition comprising an inducing agent to induce expression of a gene product in a virus-infected cell and an anti-viral agent whose anti-viral activity relates to or is directed to the expressed product. Preferably, the gene product expressed is a viral enzyme or a cellular enzyme or activity that is largely expressed in virus-infected cells. Expression products that can be targeted include enzymes involved with DNA replication, which may be either for repair or replication of the genome, assembly of complete virus particles, generation of viral membrane or walls, RNA transcription or protein translation or combinations of these activities. Interference with these process can be performed by inducing and then acting on an enzyme and, preferably, a critical enzyme in the process.

Inducing agents useful in compositions of the invention include chemical compounds of the structure $R_1$—$R_2$—$R_3$ or, preferably $R_1$—C(O)—$R_2$—$R_3$, wherein $R_1$ is $CH_X$, $H_c$, $NH_X$, $OH_X$, $SH_X$, $COH_X$, $CONH_X$, COOH or $COSH_X$; $R_2$ is $CH_X$ or a branched or linear alkyl chain; $R_3$ is $CONH_X$, $COSH_X$, COOH, $COOR_4$, $COR_4$ or $OR_4$; $R_4$ is $CH_X$, $H_X$, $NH_X$, $OH_X$, $SH_X$ or a branched or linear alkyl chain; phenyl-$R_5$–$R_6$–$R_7$ wherein phenyl is a six carbon benzyl ring or a hydrogenated, hydroxylated or halogenated six carbon ring; $R_5$ is $CH_X$, $NH_X$, $OH_X$ or $SH_X$; $R_6$ is $CH_X$, $NH_X$, $OH_X$, $SH_X$ or a branched or linear alkyl chain; $R_7$ is $CH_X$, $H_X$, $NH_X$, $OH_X$, $SH_X$, $CONH_X$, COOH, $COSH_X$, $COOR_8$, $COR_8$ or $OR_8$; $R_8$ is $CH_X$, $H_X$, $NH_X$, $OH_X$, $SH_X$ or a branched or linear alkyl chain; and phenyl-$R_9$–$R_{10}$ wherein $R_9$ is $CH_X$, $NH_X$, $OH_X$, $SH_X$ or a branched or linear alkyl chain; $R_{10}$ is $CH_X$, $H_X$, $NH_X$, $OH_X$, $SH_X$, $CONH_X$, COOH, $COSH_X$, $COOR_{11}$, $COR_{11}$ or $OR_{11}$; and $R_{11}$ is $CH_X$, $H_X$, $NH_X$, $OH_X$, $SH_X$ or a branched or linear alkyl chain; wherein x is 0, 1, 2 or 3.

Preferred examples of such compounds include propionic acid, butyric acid, succinic acid, fumaric acid monoethyl ester, dimethyl butyric acid, trifluorobutanol ($C_4H_7OF_3$), chloropropionic acid ($ClCH_2CH_2COOH$), isopropionic acid, 2-oxypentasane ($CH_3CH_2CH_2C(O)COOH$), 2,2- or 3,3-dimethyl butyric acid ($C_6H_{12}O_2$), 2,2- or 3,3-diethyl butyric acid ($C_8H_{16}O_2$), butyric acid ethyl ester, 2-methyl butanoic acid ($C_5H_{10}O_2$), fumaric acid ($C_4H_4O_3$) and amides and salts thereof. Other examples include methoxy acetic acid ($H_3C(O)CH_2COOH$), dimethyl butric acid, methoxy propionic acid, N-acetylglycine ($H_3CC(O)NCH_2COOH$), mercaptoacetic acid ($HSCH_2COOH$), 1- or 2-methyl cyclopropane carboxylic acid ($C_5H_8O_2$), squaric acid ($C_4H_2O_4$), 2- or 3-phenoxy propionic acid, methoxy butyric acid, phenoxy acetic acid, 4-chloro-2-phenoxy 2-propionic acid, 2- or 3-phenoxy butyric acid, phenyl acetic acid, phenyl propionic acid, 3-phenyl butyric acid, ethyl-phenyl acetic acid, 4-chloro-2-phenoxy-2-propionic acid, n-dimethyl butyric acid glycine amide, o-benzoyl lactic acid, o-dimethyl butyric acid lactate, cinnamic acid, dihydrocinnamic acid ($C_6H_5CHCH_3COOH$), α-methyl-dihydrocinnamic acid, thiophenoxy acetic acid, and amines, amides and salts of these chemicals.

Useful amines and amides include isobutylhydroxylamine:HCl($C_4H_{12}OCl$), fumaric acid monoamide ($C_4H_5O_2N$), fumaramide ($H_2NCOCHCHCONH_2$), succinamide and isobutyramide ($C_4H_9ON$). Salts can be sodium, potassium, calcium, ammonium, lithium or choline such as sodium 3-trimethyl silyl-1-proposulfonic acid ($C_6H_{15}O_3SiS:Na$). Sodium salts are generally undesirable because at efficacious concentrations, sodium tends to produce fluid build up and there is an eventual tissue destruction. Other salts do not have this property or, the agent of interest may be administered at lower doses, thereby minimizing any detrimental effect of sodium. Reagents which may be electrostatically or covalently bonded with the inducing agent include amino acids such as arginine (arginine butyrate), glycine, alanine, asparagine, glutamine, histidine or lysine, nucleic acids including nucleosides or nucleotides, or substituents such as carbohydrates, saccharides, lipids, fatty acids, proteins or protein fragments. Combinations of these salts with the inducing agent can also produce useful new compounds from the interaction of the combination.

Other inducing agents include retinoic acid, retinol, cytosine arabinoside, phorbols such as the phorbol diester 12–0-tetradecanoylphorbol 13-acetate (TPA), teleocidine B, indole alkaloids, cytotoxin, plant lectins from *Streptomyces*, glucocorticoids such as estrogen and progesterone, phytohemagglutinin (PHA), bryostatin, growth factors (e.g. PDGF, VEGF, EGF, FGF, NGF, TGF, BCGF), anti-sense nucleic acids (e.g. DNA, RNA or PNA), aptamers (nucleic acid oligonucleotides that form secondary or tertiary structures which bind with high affinity and selectivity to a target molecule), erythropoietin (EPO), the interleukins (IL-1, IL-2, IL-3, etc.), cAMP and cAMP analogs such as dibutyrl cAMP, activin, inhibin, steel factor, interferon, the bone morphogenic proteins (BMBs), hydroxyurea and dimethyl sulfoxide (DMSO). Other inducing agents include interferons (e.g. α-, β-, γ-interferon), cytokines such as tumor necrosis factor (TNF), cell receptors and growth factor antagonists, which may be purified or recombinantly produced.

Anti-viral agents useful in compositions of the invention include substrates and substrate analogs, inhibitors and other agents that severely impair, debilitate or otherwise destroy virus-infected cells. Substrate analogs include amino acid and nucleoside analogs. Substrates may be conjugated with toxins or other viricidal substances. Inhibitors include integrase inhibitors, protease inhibitors, polymerase inhibitors and transcriptase inhibitors such as reverse transcriptase inhibitors. Examples of nucleoside analogs include acyclovir (ACV), ganciclovir (GCV), famciclovir, foscarnet, ribavirin, zalcitabine (ddC), zidovudine (AZT), stavudine (D4T), larnivudine (3TC), didanosine (ddI), cytarabine, dideoxyadenosine, edoxudine, floxuridine, idozuridine, inosine pranobex, 2'-deoxy-5-(methylamino)uridine, trifluridine and vidarabine. Examples of a few protease inhibitors that show particular promise in human therapy include saquinivir, ritonavir and indinavir. Other anti-viral agents include interferons (e.g. α-, β-, γ-interferon), cytokines such as tumor necrosis factor (TNF), cell receptors and growth factor antagonists, which may be purified or recombinantly produced.

The particular combination of inducing agent with anti-viral agent that is most effective against a specific disorder can be determined by one of ordinary skill in the art from empirical testing and, preferably, from a knowledge of each agent's mechanism of action. Three such examples are as follows. First, many of the RNA viruses such as HIV and other retroviruses require a reverse transcriptase to transcribe their genome into DNA. A few of the agents that induce expression or activity of retroviruses and their encoded genes, such as, for example, reverse transcriptase, are known to those of ordinary skill in the art. Anti-viral agents such as nucleoside analogs can be administered to the patient. Those substrate analogs will be specifically recognized by the reverse transcriptase that, when incorporated into the infected-cell genome, result in cell death. Second, many viruses require an active protease to assemble virus capsids to be packaged with viral genome. Protease inhibitors or proteases that alter cleavage patterns so that packaging cannot occur can be specifically targeted with an anti-viral agent that comprises an amino acid analog or toxic conjugate. Third, arginine butyrate and isobutyramide enhance expression of viral thymidine kinase in EBV-infected lymphocytes. Ganciclovir or famciclovir, in the presence of the viral thymidine kinase, destroys the infected cell. Treatment of infected cells with both agents, according to the invention, will selectively destroy EBV virus-infected cells.

Compositions may be prepared in solution as a liquid, spray, capsule or as a solid such as a powder or pill, as appropriate. Many inducing and anti-viral agents can be purchased commercially and prepared as a mixed composition using techniques well-known to those of ordinary skill in the art. Others may need to be prepared from scratch or at least purified to sterility from a commercial source for human administration. For example, arginine butyrate is prepared by reacting arginine and butyric acid together, filtering the resulting product, and diluting the final solution to a fixed percentage with water, saline, glycerol, polysaccharide, oil or another relatively inert substance. Isobutyramide is prepared by reacting propionic acid with ammonia, and filtering the resulting product which is then stored at −20° C., 4° C. or room temperature, for months to years without any significant loss of activity. Solid isobutyramide can be precipitated out of solution, washed in water and crystallized. This solid form may be processed into tablet or capsule forms or mixed or dissolved with a relatively inert liquid such as water, saline, glycerol, polysaccharide or oil. Preferably, the solution is prepared as a liquid and stored without significant loss of activity for years. Filtrations can be performed using 0.45, 0.22 and 0.1 micron filters as appropriate. Sterility of these compositions are assayed using procedures which select for growth of bacteria, fungi or yeast. Sterility may also be determined by assaying for nucleic acid content using, for example, PCR (polymerase chain reaction) technology wherein particular species of nucleic acid, if present, are amplified and detected as indicators of contamination. Purities of either the liquid or solid forms are assayed by high pressure liquid chromatography (HPLC), thin layer chromatography (TLC), gas chromatography, or variations of these techniques such as fast-pressure liquid chromatography (FPLC), reverse-phase (RP) HPLC, or another method which is available to one of ordinary skill in the art. Composition are also tested, if necessary, for pyrogen using, for example, the limmulus amoebocyte lysate assay or the rabbit reticulocyte lysate assay.

Another embodiment of the invention is directed to a method for destroying, killing or otherwise severely cripple virus-infected cells by treating said cells with an inducing agent, to induce the activity of a gene product, and an anti-viral agent whose anti-viral activity is directed to the activity of the gene product induced. Preferably, the gene product is a viral enzyme that relates to a basic and necessary process of the virus such as virus adsorption, cell penetration, fusion, uncoating, reverse transcription, integration, DNA replication, viral interference, viral transcription, the switch from early to late expression, the latent or lytic phases, the switch from a latent to lytic phase, defective-interfering particle production, virus assembly, capsid packaging, the generation of virus-specific membrane, virus budding and virus secretion. The activity of one or more of these processes may be enhanced by one or more of the inducing agents and the enhanced activity targeted by one or more anti-viral agents. The combination treatment is more effective than conventional treatment with anti-viral agents alone or simply allows for the administration of therapeutically effective amounts of the anti-viral agent which are less than what would be considered effective with conventional treatment regiments.

Agents that induce expression may act directly on the viral genome or indirectly through a cellular factor required for viral expression. For example, viral gene expression can be regulated through the regulation of the expression of thymidine kinase, AP-1, AP-2, Sp1, NF-$_K$B and other transcriptional activators and/or repressors (factors), oncogenes or proto-oncogenes, or protein kinase C. These proteins act to regulate and thereby control expression of specific viral and/or other cellular genetic elements. According to the methods of the invention control over their expression can lead to control over the infection. Other gene products, both viral and cellular in origin, whose expression can be regulated with inducing agents include proteases, polymerases, reverse transcriptases, cell-surface receptors, major histocompatibility antigens, growth factors and combination of these products.

Additional genes whose expression or transcriptional regulation are altered in the presence of butyric acid includes the oncogenes myc, ras, myb, abl and src. The activities of these gene products as well as the activities of other oncogenes are described in J. D. Slamon et al. (Science 224:256–62, 1984). Anti-proliferative activity also includes the ability to repress tumor angiogenesis through the blockade of angiogenesis factor activity, production or release, transcriptional regulation, or the ability to modulate transcription of genes under angiogenesis or growth factor or hormonal control. Either would be an effective therapy particularly against both prostatic neoplasia and breast carcinomas. Further activities which effect transcription and/or cellular differentiation include increased intracellular cAMP levels, inhibition of histone acetylation, and inhibition of genomic methylation. Each of these activities are directly related to gene expression and increased expression can sensitize infected cells to a specific anti-viral agent.

Two of the preferred inducing agents are arginine butyrate and isobutyramide. Arginine butyrate induces EBV-TK activity in EBV-immortalized B-cells and patient-derived tumor cells. As latently-infected B-cells do not express TK, exposure of these cells to agents like arginine butyrate results in a modest induction of lytic replication and TK expression. Surprisingly, TK expression can be used as a point for attack by anti-viral agents allowing for treatment of latent infections.

Although there are numerous case reports of administration of inducing agents such as butyrates to patients for the treatment of malignancies (A. Novogrodsky et al., Cancer 51:9–14, 1983; A. A. Miller et al., Eur. J. Cancer Clin. Oncol. 23:1283–89, 1987), and for the administration of anti-viral agents for the treatment of viral disorders, there are no treatments directed to the administration of both agents. Arginine butyrate has been administered to adults and children over extended periods of time without major side effects (S. P. Perrine et al., Br. J. Haematol., 1994; S. P. Perrine et al., N. Engl. J. Med. 328:81–86, 1993). These drugs were recently approved for human studies to induce fetal Hb in children with sickle cell anemia and β-thalassemia. Preliminary in vitro studies demonstrate that induction of EBV-TK activity in EBV-immortalized B-cells and patient-derived tumor cells using these drugs is possible, and that these previously-resistant cells are rendered susceptible to ganciclovir therapy. Treatment of patients with viral-associated tumors such as EBV with inducing agents such as arginine butyrate, to induce the expression of EBV-TK, and GCV, to eliminate EBV-TK expressing tumor cells, is an effective, nontoxic therapy. This therapeutic regiment does not depend on the associated viral genome being the cause of the tumor. Just the presence of the EBV genome in latent form would be predicted to make the tumor susceptible to this combination protocol.

Preferably, the inducing agent is butyric acid in the form of arginine butyrate or isobutyramide and the antiviral agent is a nucleoside analog. Butyric acid is one many naturally-occurring short-chain fatty acids that are generated in the small and large bowel by metabolism of carbohydrates. Butyrate is a four-carbon fatty acid with weakly acidic properties, and is rapidly absorbed and metabolized. Butyrates have shown significant anti-tumor effects. Sodium butyrate (NAB) has been used clinically in patients with acute myelogenous leukemias and there has now been extensive experience with arginine butyrate, a salt of butyrate, in clinical studies for the treatment of β-hemoglobinopathies, and more recently with refractory solid neoplasms (F. M. Foss et al., Proc. ASCO 13:162 1994; D. A. Sanders et al., Proc. ASCO, 1995). Butyrate, and derivatives of butyrate including arginine butyrate, have demonstrated several effects upon transformed cell lines in vitro which include decreased DNA replication leading to arrest of cell division in the $G_1$ phase, modification of cellular morphology and alteration of gene expression consistent with differentiation of a given cell type examined (D. Klehr et al., Biochemistry 31:3222–29, 1992). For example, human tumor cell lines as diverse as colon, breast, melanoma, hepatoma, squamous cell carcinoma of the cervix, endometrial, adenocarcinoma, teratocarcinoma cell lines, leukemic cells (HL-60) and normal human keratinocytes can all be induced to differentiate in the presence of butyrate concentrations ranging from 2–5 mM (S. P. Perrine et al., Biochem. Biophys. Res. Commun. 148:694–700, 1987).

Multiple mechanisms of action for butyrate have been postulated. Butyrates have been shown to induce differentiation of tumor cell lines. The mechanism(s) of action proposed for these effects upon differentiation are varied, and are not fully understood. Butyrate inhibits histone (nuclear) deacetylase, which results in hyperacetylation of histones H3 and H4. When histones are acetylated, they have a reduced affinity for chromatin, thus allowing for chromosomal unfolding, and possibly enhancement of expression of certain genes. It is postulated that butyrate acts to prevent histones from binding to key regulatory regions on chromatin designated as nuclear scaffolding attached regions, and nuclear matrix-attached regions, with a net result that promoter regions of certain genes are exposed for expression.

Butyrate-associated induction of genes have been characterized for various cell types, and the genes are consistently in the class of differentiation markers of a cell. For example, in colon cancer cell lines, morphologic changes observed in the presence of butyrate correlate with increased expression of alkaline phosphatase, plasminogen activator and CEA, all markers of differentiation. Hepatoma cell lines increase expression of alpha fetoprotein. Breast cancer cell fines express milk-related glycoproteins, epithelial membrane antigens and increased lipid deposition. Sodium butyrate can also induce expression of cellular proteins associated with converting basal keratinacytes into committed epithelial cells.

Alteration of expression of certain transcription factors that regulator gene expression and regulation of the cell cycle. In the breast cancer cell line MCF-7, butyrate induces a block in cellular proliferation which is associated with decreased expression of estrogen and prolactin hormone receptor mRNA expression, thus blocking the potential growth stimulation by estrogen and prolactin. These effects are associated with increased expression of the EGF receptor. Butyrate also has been shown to induce down regulation of c-myc and p53 mRNA, and up-regulate expression of the c-fos transcription factor. In mouse fibroblasts, butyrate will block the cell cycle in the G1 phase. When these cells are stimulated to proliferate with serum, TPA or insulin, the immediate-early response transcription factors c-myc and c-jun are unregulated. However, the late G1 phase downstream gene marker cdc-2 mRNA is not expressed and cells are prevented from entering S phase.

Butyrate is an effective cell cycle blocker, associated with a putative restriction point, related to termination of expression of a labile protein. It is generally thought to block cell cycle progression in G1, but might also inhibit some cell types at a point in G2 (J. H. Bruce et al., Neurochem. Res. 17:315–20, 1992). Decreased p53 levels in correlation with butyrate treatment and the inhibition of polyomavirus DNA replication in p53 and Rb-knockout primary mouse fibroblasts in response to butyrate appear to rule out a direct involvement of these gene products individually in the mechanism of butyrate and imply that a putative control point perhaps lies at a later step in the cell cycle. It therefore appears that the butyrate effect is likely to involve a mechanism fundamentally conserved among cell types, but it does not appear to be exerted directly via the Rb or p53 gene product.

The herpes virus family members are capable of bypassing the butyrate-mediated block, which is probably due to the role of viral early genes in DNA synthesis, such as the viral DNA polymerase, DNA-binding protein and helicase genes (F. F. Shadan et al., J. Virol. 68:4785–96, 1994). Butyrate treatment has been reported to result in the induction of the major CMV major immediate-early protein (IEP) by activating the IEI promoter via cellular factors in a human epithelial thyroid papilloma carcinoma cell line, and in cultured endothelial cells 149 under conditions that are conducive to terminal differentiation (L. P. Villarreal, Microbiol. Rev. 55:51242, 1991). Similarly, EBV early antigen is induced by butyrate in the P3HR-1 cell line as well as Raji and NC37 cell lines. These results indicate that butyrate exerts some of its effects on viral growth at the level of gene transcription. This conclusion is also supported by the observation that butyrate activates the long terminal repeat-directed expression of human immunodeficiency virus and induces the Moloney murine sarcoma virus via a putative butyrate response enhancer-promoter element (C. Bohan et al., Biochem. Biophys. Res. Commun. 148:899–907, 1987; D. C. Tang et al., Biochem. Biophys. Res. Commun. 189:141–47, 1992; A. Yeivin et al., Gene 116:159–64, 1992). Therefore, butyrate appears associated with a general induction of early viral proteins. Butyrate has been reported to exert additional cytostatic effects such as G2/M blockage and anti-viral activity against RNA viruses.

One of the more difficult viral disorders to treat is a herpes virus infection. These viruses manifest distinct pathologies for both the active or lytic phase, and the latent phase. Many herpes-family virus-infected cells, including many cells infected by HSV and CMV, can be killed by nucleoside analog antiviral drugs like ganciclovir and acyclovir. Epstein-Barr virus (EBV), a typical herpes virus, is at best slightly susceptible to anti-viral drugs that inhibit replication of the herpes viruses. These drugs are not effective in limiting the progress of the disease, and, moreover, do not cure the underlying infection. Infectious particles remain in local regions of the body and susceptibility to anti-viral drugs is too difficult to assess as there is no adequate in vitro system for studying lytic replication. There are also no plaque assays for EBV and efficient in vitro infection of epithelial cells followed by lytic replication does not occur.

Unlike other members of the herpesvirus family, EBV is resistant to the antiviral agent ganciclovir, because of low levels of viral thymidine kinase. Acyclovir and ganciclovir have also been used to treat AIDS patients, many of whom had an active EBV infection. During treatment, regression of hairy leukoplakia, an EBV disorder, was inadvertently observed while latent EBV infection was unaffected. Additional studies demonstrated that even when virus production is minimal, expression of many EBV genes, active during the lytic cycle such as thymidine kinase, can be induced. Therefore, exposure of EBV-transformed B-cells or tumor cells to arginine butyrate induces EBV-TK and renders them sensitive to ganciclovir.

Like herpes simplex virus (HSV) and varicella-zoster virus (VZV), EBV encodes a thymidine kinase enzyme localized to the BamH I, X fragment of the genome. In a rate-limiting step, the TK converts nucleoside analogs to their monophosphate form. Cellular enzymes complete their conversion to biologically-active triphosphates. A viral DNA polymerase preferentially incorporates the toxic metabolites into viral DNA, leading to premature termination of the nascent DNA. ACV is a purine nucleoside analog with a linear side chain replacing the cyclic sugar of guanosine. GCV differs from ACV in the addition of a hydroxymethyl group to the side chain. However, ACV and GCV differ in functional assays. Whereas HSV TK preferentially phosphorylates ACV, EBV-TK preferentially phosphorylates GCV. Furthermore, because GCV triphosphate accumulates to higher levels and persists for longer periods in infected cells than ACV, GCV produces more interference with cellular DNA synthesis than occurs with ACV. In one study, selective toxicity of GCV for cells expressing HSV-TK was utilized to promote tumor killing in the CNS. Rapidly dividing murine glioma cells were infected in vivo with an amphotropic retrovirus containing HSV-TK. Animals were treated with GCV, which killed TK+ tumor cells, sparing adjacent normal cells that replicated too slowly for efficient infection and viral TK expression.

Types of virus infections and related disorders that can be treated include, for example, infections due to the herpes family of viruses such as EBV, CMV, HSV I, HSV II, VZV and Kaposi's-associated human herpes virus (type 8), human T cell or B cell leukemia and lymphoma viruses, adenovirus infections, hepatitis virus infections, pox virus infections, papilloma virus infections, polyoma virus infections, infections due to retroviruses such as the HTLV and HIV viruses, and infections that lead to cell proliferative disorders such as, for example, Burkitt's lymphoma, EBV-induced malignancies, T and B cell lymphoproliferative disorders and leukemias, and other viral-induced malignancies. Other neoplasias that can be treated include virus-induced tumors, malignancies, cancers or diseases which result in a relatively autonomous growth of cells. Neoplastic disorders include leukemias, lymphomas, sarcomas, carcinomas such as a squamous cell carcinoma, a neural cell tumor, seminomas, melanomas, germ cell tumors, undifferentiated tumors, neuroblastomas (which are also considered a carcinoma by some), mixed cell tumors or other malignancies. Neoplastic disorders prophylactically or therapeutically treatable with compositions of the invention include small cell lung cancers and other lung cancers, rhabdomyosarcomas, chorio carcinomas, glioblastoma multiformas (brain tumors), bowel and gastric carcinomas, leukemias, ovarian cancers, prostate cancers, osteosarcomas or cancers which have metastasized. Diseases of the immune system which are treatable include the non-Hodgkin's lymphomas including the follicular lymphomas, adult T and B cell lymphoproliferative disorders such as leukemias and lymphomas, hairy-cell leukemia, hairy leukoplakia, acute myelogenous, lymphoblastic or other leukemias, chronic myelogenous leukemia and myelodysplastic syndromes. Additional diseases which can be treated include breast cell carcinomas, melanomas and hematologic melanomas, ovarian cancers, pancreatic cancers, liver cancers, stomach cancers, colon cancers, bone cancers, squamous cell carcinomas, neurofibromas, testicular cell carcinomas, and adenocarcinomas.

Viruses may exist in infected cells as autonomous particles, or be integrated as, for example, latent infections. Latent infections may be periodic, such as HSV I and II, or be continuously productive of virus or virus products, but at fairly low levels. Infections may also be lytic with infectious particles secreted or otherwise extruded or expelled (virus burst) from cells. Infections may also be of parts of a virus such as, for example, by viral genes or by defective-interfering particles which are incapable of productive replication on their own, but may be capable of causing disease.

Cells that can be treated include any cell that becomes infected with a virus or a part of a virus and, preferably, infected by integration. Such cells include cells of the hematopoietic system such as lymphocytes, erythrocytes and mylocytes, neural cells and neural-supporting cells, cells of the digestive system, cells of the epithelial system. Cells that contain integrated viral genomes or only parts of viral genomes may also be effectively treated.

Administration of the inducing agent and the antiviral agent may be to cells or directly to a patient for prophylaxis or therapeutic treatment of a confirmed or suspected viral disorder. The patient may be a domesticated animal or mammal such as a dog, cat, horse, cow, steer, pig, sheep, goat or chicken, or a wild animal, but is preferably a human. Administration may be to an adult, an adolescent, a child, a neonate, an infant or in utero.

Administration of the inducing agent and the anti-viral agent may be staggered over time or simultaneous in a single composition. Administration of either agent may be short term, continuous or sporadic as necessary. Patients with a suspected or diagnosed viral-associated disorders may only require treatment for short periods of time or until the disorder has been effectively overcome.

Methods of administration may involve oral, parenteral, sublingual, rectal or enteral administration, or pulmonary absorption or topical application of inducing agent and anti-viral agent which may be co-administered or administered in any order. Parenteral administration may be by intravenous injection, subcutaneous injection, intramuscular injection, intra-arterial injection, intrathecal injection, intra peritoneal injection or direct injection or other administration to the site of the neoplasm. Injectable forms of administration are sometimes preferred for maximal effect. When long term administration by injection is necessary mediports, in-dwelling catheters, or automatic pumping mechanisms are also preferred wherein direct and immediate access is provided to the arteries in and around the heart and other major organs and organ systems.

An effective method of administration to a specific site may be by transdermal transfusion such as with a transdermal patch, by direct contact to the cells or tissue, if accessible, such as a skin tumor, or by administration to an internal site through an incisions or some other artificial opening into the body. Compositions may also be administered to the nasal passages as a spray. Diseases localized to the head and brain area are treatable in this fashion as arteries of the nasal area provide a rapid and efficient access to the upper areas of the head. Sprays also provide immediate access to the pulmonary system and are the preferable methods for administering compositions to these areas. Access to the gastrointestinal tract is gained using oral, enema, or injectable forms of administration. Compositions may be administered as a bolus injection or spray, or administered sequentially over time (episodically) such as every two, four, six or eight hours, every day (QD) or every other day (QOD), or over longer periods of time such as weeks to months.

Orally active compositions are preferred as oral administration is usually the safest, most convenient and economical mode of drug delivery. Oral administration is usually disadvantageous because compositions are poorly absorbed through the gastrointestinal lining. Compounds which are poorly absorbed tend to be highly polar. Consequently, compounds which are effective, as described herein, may be made orally bioavailable by reducing or eliminating their polarity. This can often be accomplished by formulating a composition with a complimentary reagent which neutralizes its polarity, or modifying the compound with a neutralizing chemical group. Oral bioavailability is also a problem because drugs are exposed to the extremes of gastric pH and gastric enzymes. These problems can be overcome in a similar manner by modifying the molecular structure to be able to withstand very low pH conditions and resist the enzymes of the gastric mucosa such as by neutralizing an ionic group, by covalently bonding an ionic interaction, or by stabilizing or removing a disulfide bond or other relatively labile bond.

When the composition is administered orally, it may be in the form of a liquid, a pill, a tablet or a capsule. Liquids administered orally may include flavoring agents such as mint, cherry, guava, citrus, cinnamon, orange, mango, or mixed fruit flavors. Pills, capsules or tablets administered orally may also include flavoring agents. Additionally, all compositions may further comprise agents to increase shelf-life, such as preservatives, anti-oxidants and other components necessary and suitable for manufacture and distribution of the composition.

Compounds may also be used in combination with other agents to maximize the effect of the compositions in an additive or synergistic manner. Cytokines which may be effective in combination with the compositions of the invention include growth factors such as B cell growth factor (BCGF), fibroblast-derived growth factor (FDGF), granulocyte/macrophage colony stimulating factor (GM-CSF), granulocyte colony stimulating factor (G-CSF), macrophage colony stimulating factor (M-CSF), epidermal growth factor (EGF), vascular endothelial growth factor (VEGF), platelet derived growth factor (PDGF) nerve growth factor (NGF), stem cell factor (SCF), and transforming growth factor (TGF). These growth factors plus a composition may further stimulate cellular differentiation and/or the expression of certain MHC antigens or tumor antigens. For example, BCGF plus a composition may be effective in treating certain B cell leukemias. NGF plus a composition may be useful in treating certain neuroblastomas and/or nerve cell tumors. In a similar fashion, other agents such as differentiating agents may be useful in combination with a composition of the invention to prevent or treat a neoplastic disorder. Other differentiating agents include B cell differentiating factor (BCDF), erythropoietin (EPO), steel factor, activin, inhibin, the bone morphogenic proteins (BMPs), retinoic acid or retinoic acid derivatives such as retinol, the prostaglandins and TPA.

Alternatively, other cytokines and related antigens in combination with a composition may also be useful to treat or prevent certain virus infections and other viral disorders. Potentially useful cytokines include tumor necrosis factor (TNF), the interleukins IL-1, IL-2, IL-3, IL-4, IL-5, IL-6, etc., recombinant IL receptors, growth factors, colony stimulating factors, erythropoietin (EPO), the interferon (IFN) proteins IFN-α, IFN-β, and IFN-γ; cyclic AMP including dibutyryl cyclic AMP, hemin, DMSO, hydroxyurea, hypoxanthine, glucocorticoid hormones and cytosine arabinoside. Therapies using combinations of these agents would be safe and effective therapies against malignancies and other forms of cancer. Combinations of therapies may also be effective in inducing regression or elimination of a tumor or some other form of proliferative disorder such as compositions of the invention plus radiation therapy, toxin or drug conjugated antibody therapy using monoclonal or polyclonal antibodies directed against the transformed cells, or specific anti-sense therapy. Effects may be additive, logarithmic or synergistic, and methods involving combinations of therapies may be simultaneous protocols, intermittent protocols or protocols which are empirically determined.

Compositions and methods for the treatment of viral disorders, and particularly viral proliferative disorders, by augmenting the treatment methods of the invention with conventional chemo-therapy, radiation therapy, antibody therapy, and other forms of therapy. Some conventional chemotherapeutic agents which would be useful in combination therapy with methods and compositions of the invention include the cyclophosphamide such as alkylating agents, the purine and pyrimidine analogs such as mercaptopurine, the vinca and vinca-like alkaloids, the etoposides or etoposide like drugs, the antibiotics such as deoxyrubocin and bleomycin, the corticosteroids, the mutagens such as the nitrosoureas, antimetabolites including methotrexate, the platinum based cytotoxic drugs, the hormonal antagonists such as antiinsulin and antiandrogen, the antiestrogens such as tamoxifen an other agents such as doxorubicin, L-asparaginase, DTIC, MAMSA, procarbazine, hexamethylmelamine and mitoxantrone. These agents could be given simultaneously or alternately as defined by a protocol designed to maximize effectiveness, but minimize toxicity to the patient's body.

Virus-infected cells may also be treated in vivo by administering the inducing agent and the anti-viral agent directly to the patient. For example, patients exposed to mutagens, carcinogens, radiation, or other cancer producing agents may be continuously treated with compositions to inhibit the expected development of a neoplastic condition. Patients who have been genetically screened and determined to be at high risk for the future development of a neoplasia may also be administered compositions, possibly beginning at birth and possibly for life. Both prophylactic and therapeutic uses are readily acceptable because these compounds are generally safe and non-toxic at effective dosages.

Another embodiment of the invention is directed to a method for treating a viral disorder in a patient comprised of administering an activator and an anti-viral agent to the patient wherein the activator is administered in an amount sufficient to activate expression of a latent virus integrated into proliferating cells of the patient. Useful activators include phorbol ester, an oxidized phorbol ester, ceramide, bryostatin, an inducing agent or a combination thereof. Activator should be administered in an amount sufficient to activate, for example, protein kinase C, an oncogene, thymidine kinase, AP-1, AP-2, Sp-1 or NF-$_K$B.

The following examples illustrate embodiments of the invention, but should not be viewed as limiting the scope of the invention.

EXAMPLES

Example 1 Clinical Toxicity and Pharmacology.

Clinical experience with butyrates have been performed in children with acute myelogenous leukemia in Israel, and in children with neuroblastoma (K. Prasad, Life Sci. 27:1351–58, 1980). Doses of sodium butyrate ranging from 0.5–1.5 g/kg/day for 14 days, and 10 g/kg/day IV infusions were given without toxic side effects. IV infusion of similar doses of sodium and arginine butyrate in adults resulted in no toxic side effects, and elevated plasma butyrate levels returned to normal within 15 minutes of discontinuation. Eleven pediatric patients and twelve adults with β-hemoglobinopathies were treated with IV arginine butyrate at a starting dose of 500 mg/kg/day for 2–7 weeks. If no side effects were noted, the rate was increased by 250 mg/kg/day to a final rate of 1500 mg/kg/day in 4 patients, and 2000 mg/kg/day in 2 patients. Side effects were a transient, slight rise in serum aminotransferase in a patient with sickle cell disease. This same patient, and one other also, had a brief blood urea nitrogen, but not creatinine, at the end of a continuous infusion over 2 weeks. This rise in BUN returned to normal within 12 hours of discontinuation of drug, and is thought to be secondary to effect of arginine upon ureagenesis. Transient anorexia developed in one patient. Peak serum levels of butyrate ranged between 0.04–0.05 mM, and butyrate was not detectable 15 minutes after infusion was discontinued. Plasma arginine levels were also rapidly cleared, with a $T_{1/2}$ of 15 minutes, and baseline arginine levels were reached within 12 hours after discontinuation of infusion.

Three patients with refractory neoplasms (breast, melanoma, adenocarcinoma, of unknown primary) have been enrolled and completed 1–2 cycles of arginine butyrate as a dose of 500 mg/kg/day over 6–8 hours for 10 days. There were no objective toxicities noted for the hepatic, renal, cardia, pulmonary or hematopoietic systems. Two of three patients experienced grade 1 nausea/vomiting which was controlled with oral anti-emetics. No objective tumor responses were noted.

Three patients (with breast cancer, bowel cancer or Hodgkins disease) have completed two cycles of arginine butyrate at a dose of 750 mg/kg/day for 10 days. One of the three patients had grade I nausea/vomiting which was controlled with oral anti-emetics. One patient had a transient elevation of serum BUN without elevation of serum Cr, and discontinuation of the drug. Otherwise, there was no other objective measures of organ progressed after treatment was topped. One patient had a partial response (>80%) after first cycle, with resolution of lymphadenopathy and leukocytosis, and complete resolution of back pain, with all narcotics stopped. There was a further resolution of the disease during the second cycle. Disease progression was noted one month after second cycle was completed. At 1000 mg/kg/day, 3 patients have been enrolled on study.

Example 2 Drug Formulation and Availability.

Butyric acid is a short chain fatty acid present in foods such as dairy products. Arginine is an amino acid which is commonly used in hyperalimentation solutions in hospitals throughout the country. Butyric acid was obtained from Aldrich, catalog number W-212. L-Arginine is anhydrous. Arginine was combined with butyric acid, pH 5.0–5.5, in sterile, non-pyrogenic water for injection to neutralize the fatty acid. The solution was filtered through a Millipore System at a final concentration for injection of 100 mg/ml or 25 mg/ml. Each lot was pyrogen tested and tested for sterility and purity. Stability testing has demonstrated stability in glass containers up to 404 days. Since 10% arginine butyrate solution is hypertonic (100 mg/ml), it must be infused through a long or deep IV access to avoid peripheral venous irritation. Arginine butyrate was infused via an infusion pump. European pharmacokinetic studies of arginine butyrate given as a "slow" and 90 minute bolus of 500 mls of a 5% solution (2.5 g/M in two normal volunteers, and found a 15 minute elimination period. Plasma levels from patients with hemoglobinopathies have shown that butyric acid disappears within 5 to 15 minutes after an infusion of up to 2,000 mg/kg/day.

Example 3 Study Synopsis.

This is an intra-patient dose escalation study designed to enroll up to 10 patients with EBV+ neoplasms. The major objectives are to evaluate the safety and pharmacology of arginine butyrate given in combination with ganciclovir (GCV). Because of the paucity of patients with EBV malignancies, this study employees intra-rather than inter-patient dose escalation. Because of the clinical experience already available with arginine butyrate, it is felt that this design will permit selection of a safe and effective dose regimen for a study in the future.

In vitro, peaks induction of EBV-TK plateaus at serum level of around 1 mM. In Phase I studies, doses of 1,000 mg/kg/day have resulted in serum levels of 0.5 to 0.75 mM. Therefore, dose levels up to 2,000 mg/kg/day, were evaluated in an attempt to reach serum levels of 1 mM. Treatment cycles were of 4 week duration, with 3 weeks on treatment and one week off. Patients were given the standard dose of GCV throughout each 21 day course of arginine butyrate, starting, however, on day 0. Arginine butyrate was given by continuous IV infusion at 500 mg/kg/day for 2 days, at 1,000 mg/kg/day for 2 days, at 1,500 mg/kg/day for 2 days, and thereafter at 2,000 mg/kg/day, or as tolerated, for the rest of the 21 day course. Cycle 2 was begun on Day 29. Patients were given a complete tumor evaluation after every course with subsequent cycles emitted unless disease progressed.

Example 4 Patient Selection.

All patients selected had a microscopically documented neoplasm, (which if B-cell lymphoid, was monoclonal or oligoclonal, but not polyclonal), and EBV (+) as determined by immunohistochemistry [EBNA-2(+) and/or LMP-1(+)] and/or in situ hybridization [EBER + (EcoR I J] or [internal repeat + BamFH W(+)] or [EBNA-1 +(BamM K(+)]. Serology for EBV was obtained from each patient (and preferably from donor in the transplant setting), but need not be EBV(+). Patients with evaluable tumor are preferred. Patients with EBV-LPD who have not had prior cytotoxic chemotherapy or radiotherapy for this disease are preferred. Since there is no effective therapy for EBV-LPD, prior therapy was not required.

With respect to other EBV-associated malignancies, all patients had been refractory to at lease one combination of chemotherapy regimen, and were considered incurable by standard therapy. Patients should have recovered from prior chemotherapy or radiotherapy. At least 3 weeks elapsed since the last course of chemotherapy (6 weeks for nitrosoureas or mitomycin C). Minimum hematologic requirements were a platelet count greater than 30,000/mm³. Patients had a serum bilirubin less than 3.0 mg/dl, serum aminotransferase less than 2 times normal, and serum creatinine of less than 3.0 mg/dl. The calculated creatirline clearance was greater than 30 ml/minute. Patients had not had an acute myocardial infarction, or onset of atrial fibrillation within 6 months of study, were HIV negative and had the ability to give informed consent.

Example 5 Treatment Plan Including Dosing.

Eligible patients were provided central venous access via Porta-Cath or Ffickman line because of the hyperosmolarity of the arginine butyrate solution. On days 3 to 1 treatment with ganciclovir alone at standard doses (5 mg/kg IV over 1 hour bid) were given (unless already ongoing) and were continued through day 21. On day 1, infusion of arginine butyrate were begun at a total starting dose of 500 mg/kg/day to be infused continuously. In the absence of intolerable toxicity, dose escalation of arginine butyrate was according to the following scheme:

Level 1: 500 mg/kg/day IV (20.8 mg/kg/hr) for 2 days.
Level 2: 1000 mg/kg/day IV (41.6 mg/kg/hr) for 2 days.
Level 3: 1500 mg/kg/day IV (62.5 mg/kg/hr) for 2 days.
Level 4: 2000 mg/kg/day IV (83.2 mg/kg/hr) as tolerated and continued for the remainder of the 21 day treatment cycle.

Serum was obtained pretreatment and 4 hours into infusion on days 1, 3, 5, 7, 14 and 21 of treatment for measurement of butyrate levels. Serum samples were obtained at 30 minutes, 1 hour, 2 hours, 4 hours, 8 hours and 24 hours after discontinuation of infusion. Pretreatment and on days 2, 4, 6 and 8 of treatment, urine were collected for measurement of butyrate levels.

Arginine butyrate infusion was continued to and throughout day 21 and was discontinued as well GCV. Patients were examined on day 21 and serum was obtained for renal, hepatic and hematologic function. Repeat staging and biopsy (if tumor peripherally accessible) was done during the fourth week of each cycle. For patients that demonstrated stable disease, up to three cycles of treatment were given. If there is disease progression, or intolerable toxicity, the patient will be removed from the protocol. If a patient experiences a PR, up to six cycles may be given. If a patient experiences a CR, additional cycles may be given. Therapy in individual patients will be discontinued at any dose level if unacceptable drug-related toxicity occurs. Adverse drug reaction guidelines will be observed for reporting toxicity.

Example 6 Clinical Pharmacology.

All patients entered undertook a pharmacokinetic study. This was to detect whether dose-dependent pharmacokinetics occur and whether drug levels or area under the curve correlate with toxicity. Blood samples of approximately 2 ml were collected in heparinized tubes. These samples were collected during the first cycle at pretreatment and on days 1, 3, 5, 7, 14 and at the end of infusion and at 30 minutes, 1 hour, 2 hours, 4 hours, 8 hours and 24 hours post-treatment. Plasma from these samples were separated by centrifugation, immediately frozen and stored at $-20°$ C. until analyzed.

Aliquots of urine (approximately 25 ml) were collected during the first cycle pretreatment, and days 2, 4, 6 and 8 of treatment. Urine was promptly frozen and stored at $-20°$ C. until analyzed.

At the discretion of the principal investigator tumor tissue samples from effusions, malignant ascites, blood or easily accessible tumor tissue were obtained pre-treatment and post-treatment (as standard care of routine evaluation and staging of patients with cancer).

Example 7 Response Criteria.

All tumor measurements were recorded in centimeters and consisted of the longest tumor diameter and the longest perpendicular diameter. Liver size measurements were recorded at the xiphoid line and in the right MCL. Definitions of response:

Complete Emnse (CM Disappearance of all evidence of active disease for a minimum of 4 weeks. The patient must be free of any symptoms related to cancer. AU lytic lesions must have remineralized. No new lesions can have occurred.

Partial response (PR): 50% or greater decrease in the sum of the products of perpendicular diameters of measurable lesions for a minimum of 4 weeks. No simultaneous increase in size of any lesion or appearance of any pew lesion may occur. For tumors which can only be measured in one dimension, a greater than 50% shrinkage in largest dimension will quality as a PR.

Minor response (MR): Objective regression of measurable lesions of greater than 25%, but less than 50% for a minimum of 4 weeks. No simultaneous increase in size of any lesion or appearance of any new lesion may occur.

Stable disease (SD): Steady state of disease; less than minor response, without progression. There may be no appearance of new lesions or worsening of cancer-related symptoms. This state must be maintained for a minimum of eight weeks to qualify for disease stability.

Progressive disease (PD): Increase of at least 25% in the size of measurable lesions, or clearly progressive skeletal involvement manifested by new lytic lesions. For patients in partial remission, an increase of 25% or more in the sum of the products of the diameters of all measured tumors over that which was obtained at the time of maximum response or the appearance of any new lesions.

Relapse: The development of any new lesions or regrowth of old lesions in patients who achieved a complete response.

Duration of response (CR and PR) will be measured from the beginning of treatment to the first sign of progression or relapse. Duration of survival shall be determined from the time of the tissue diagnosis.

Example 8 Toxicity and Pharmacology.

No organ specific toxicity was recorded by any principal investigator. There were also no drug-related deaths or life-threatening events (grade 4) due to drug administration. Pre-clinical data on the anti-neoplastic properties of arginine butyrate was divided into three areas: 1) induction by arginine butyrate of gene products in neoplastic cells which lead to differentiation of neoplastic cells, and thus, inhibition of their growth, or induction of gene products which lead to increased susceptibility to therapy directed to the induced gene product; 2) direct cytotoxic activity of arginine butyrate and cytotoxic activity in combination with chemotherapy to human tumor lines which display acquired drug resistance; 3) cytotoxic activity of combination therapy with arginine butyrate and ganciclovir on EBV+tumors.

Example 9 Induction of Differentiation and Gene Induction by Arginine Butyrate.

One current theory about the biology of cancer is that it represents an arrest in the development of the cell. The cancer cell remains in a relatively immature state and continues to be capable of growth and replication. A normal cell would mature fully into a functional bowel cell, blood cell, lung cell, etc, and would no longer be capable of growth. This process is called differentiation, and a cancer cell would therefore be a cell which has not differentiated fully (possibly as a result of oncogene activation). In theory, agents which can force the cancer cell to complete differentiation would render it incapable of further growth. Agents which can force differentiation of leukemia cells in vitro (cytosine arabinoside, retinoic acids, etc.) have recently been used effectively in patients to turn leukemia cells into normal, mature-appearing cells with a concordant slowing of the course of the disease.

Butyric acid is known for its ability to force differentiation of (human) erythroleukemia cells, chronic myelogenous leukemia cells (A. Novogrodsky et al., Cancer 51:9–14, 1983; Y. S. Chung et al., Cancer res. 45:2976–82, 1985), bowel cancer cells (A. B. Awad et al., Nutr. Cancer 16:125–33, 1991; L. Garnet et al., Int. J. Cancer 52:286–89, 1992). keratinocytes, salivary adenocarcinoma cells, pancreatic adenocarcinoma cells, melanoma cells, ovarian adenocarcinoma cells, medullary thyroid carcinoma cells, uterine malignancy cells, Burkitt lymphoma cells, germ cell malignancies, breast cancer cells, astrocytoma cells, hepatoma and neuroblastoma cells. The mechanisms whereby butyrate forces differentiation of tumors and an arrest in their growth are not fully understood, but butyrate's activity in increasing intracellular levels of cAMP, inhibiting histone acetylation, and inhibiting methylation of genomic DNA may be related to its differentiation effects. In many cases, this differentiation is accompanied by down-regulation of activated oncogenes in the tumors.

Butyric acid has not been tested extensively in humans because of the lack of an acceptable formulation. Clinical use of sodium butyrate require large doses because of the short half-life; results in salt overload and causes venous irritation.

A formulation with arginine was developed that prevents the salt overload, decreases venous irritation and possesses a longer half-life. The ability of arginine butyrate to induce differentiation has been evaluated and is measured by inhibition of growth, in some of the neoplastic cell types previously reported to be sensitive to (sodium) butyric acid, and found arginine butyrate to be as potent as butyric acid. We have also extended that work to additional cell types and found Arginine Butyrate to induce differentiation in these new cell types. Table 1 lists the cell types tested and the minimum inhibitory concentration (MIC) of sodium butyrate (NaB) and arginine butyrate (ArgB) on these cell lines. The MIC is the lowest dose that prevents all growth over the 7 days that the cells are maintained in culture, that is the minimum dose that prevents an increase in cell number. While the MICs of NaB and ArgB was above 5 mM on normal cells, their MIC was below 0.5 mM on 4 of 8 tumor lines, and below 5 mM on all but one tumor line. The WC of ArgB and NaB were equivalent on all cell lines tested.

TABLE 1

MIC of Sodium Butyrate (NaB) and Arginine Butyrate (ArgB) On Normal Human and Human Tumor Cell Line Proliferation

| Cells and Cell Lines | Compound | MIC |
|---|---|---|
| Non-Tumor: | | |
| Fibroblasts (normal human) | NaB | >5,000 μM |
| | ArgB | >5,000 μM |
| Fibroblasts (mouse BALB/c-3T3) | NaB | >5,000 μM |
| | ArgB | >5,000 μM |
| Human Tumors: | | |
| Rhabdomyosarcoma | NaB | 156 μM |
| | ArgB | 156 μM |
| Osteosarcoma (HOS) | NaB | 312 μM |
| | ArgB | 312 μM |
| Choriocarcinoma (JAR) | NaB | 156 μM |
| | ArgB | 156 μM |
| Glioblastoma Multiforme | NaB | N.D. |
| | ArgB | 1,000 μM |
| Colonic Adenocarcinoma (HT29) | NaB | 2,000 μM |
| | ArgB | 2,000 μM |

TABLE 1-continued

MIC of Sodium Butyrate (NaB) and Arginine Butyrate (ArgB) On Normal Human and Human Tumor Cell Line Proliferation

| Cells and Cell Lines | Compound | MIC |
|---|---|---|
| Gastric Carcinoma (AGS) | NaB | 2,000 μM |
| | ArgB | 2,000 μM |
| Myeloid Leukemia (HL60) | NaB | 78 μM |
| | ArgB | 78 μM |
| Erythroleukemia (K562) | NaB | >5,000 μM |
| | ArgB | 1,250 μM |

Human neuroblastoma cell line SK-N-MC was studied under different conditions. In this case, the cells were grown for 4 weeks with continuous exposure to sodium butyrate or arginine butyrate, and the cell number was quantitated at the end of this time. As shown in Table 2, a dramatic decrease in cell growth was observed after treatment with arginine butyrate, at levels of drug readily achieved in plasma. The expression of the oncogene n-myc transcript was decreased approximately Mold in neuroblastoma cells treated with arginine butyrate (1 mM) compared to normal cells.

TABLE 2

Effect of Arginine Butyrate on Proliferation of Human Neuroblastoma Cell Line, SK-N-MC

| Compound | Concentration | Cell Number |
|---|---|---|
| No treatment | — | $1 \times 10^8$ |
| Arginine Butyrate | 0.05 mM | $1 \times 10^5$ |
| Arginine Butyrate | 1.0 mM | $<1 \times 10^3$ |

Figure 1B:
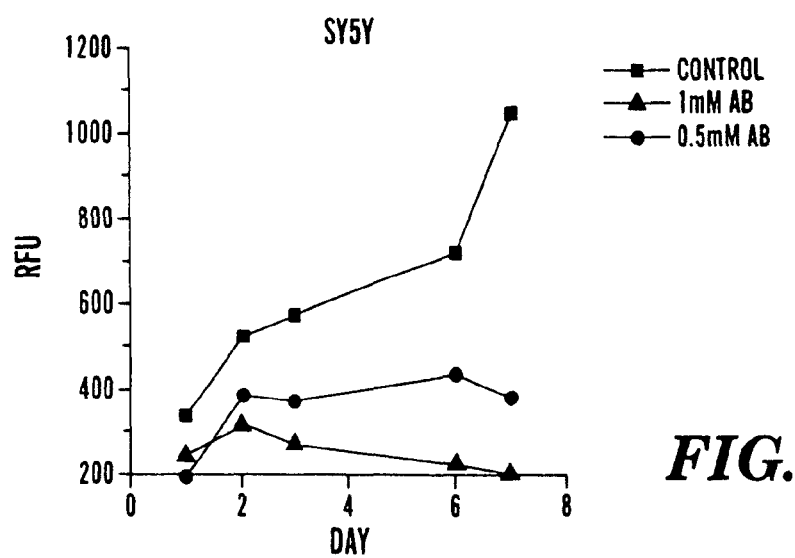
Figure 1C:
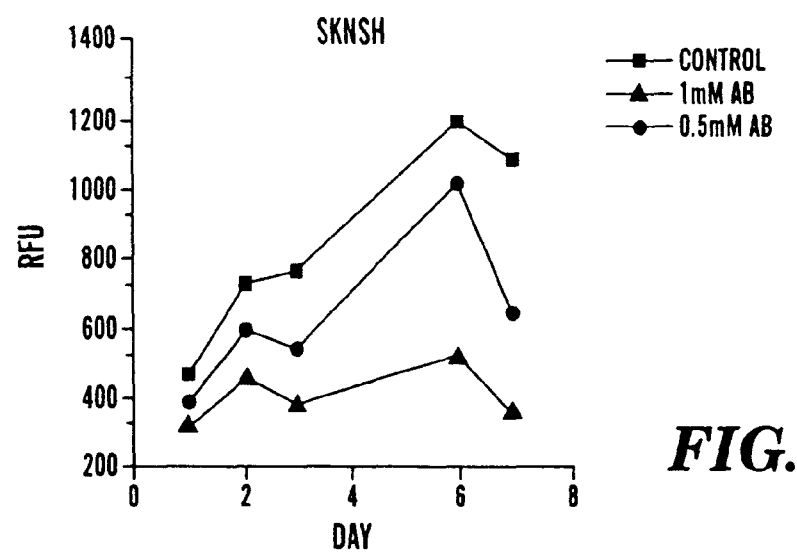

Similar growth inhibition studies but over 6 days rather than 4 weeks, were performed or 3 other neuroblastoma cell lines. As shown in FIG. 1a, all three cells lines showed dose response growth inhibition to the two concentrations, 0.5 and 1.0 mM of arginine butyrate tested (RFU=relative fluorescent units which is proportional to the number of live cells as described in Ginis and Faller, Anal. Biochem. 219:288–96, 1994). Arginine butyrate also induces apoptosis in SKNSH cells (FIG. 1b) and the SY5Y neuroblastoma cell line (FIG. 1c).

The effects of arginine butyrate compounds on differentiation of several human tumor cell lines were evaluated by visual inspection and by histochemical and pathological staining:

Myeloid Leukemia (HL60): These cells responded to arginine butyrate analogues by differentiation along myeloid lines, acquiring a number of characteristics of mature, terminally differentiated neutrophils, including morphology identical to a mature neutrophil, expression of myeloperoxidase, specific esterases and the capacity to generate an oxidative burst.

Erythroleukemia (K562): These cells acquired the capacity to synthesize globin mRNA and protein and hemoglobin, like a normal red blood cell, and became red in color.

Colonic Adenocarcinoma (HT 29): Arginine butyrate produced absolute growth arrest by day 3–4, with no further growth out to 25 days. Inhibition of DNA synthesis (as measured by $^3$H-thymidine incorporation) occurred by 6 hours. Expression of the proto-oncogene c-myc was decreased by 2 hours. Morphologically, the treated cells developed a mature brush border, and increased expression of sucrase/isomaltase.

Gastric Carcinoma (AGS): These cells began to express mucin after treatment with Arginine Butyrate, a marker of mature gastric cell. Although HLA antigens are expressed on normal, fully differentiated cells, they are not expressed or are minimally expressed on most neoplastic cells. In this way neoplastic cells escape recognition by the cellular arm of the immune system and are able to survive.

HLA Induction: Arginine butyrate was tested for its ability to induce expression of HLA antigens in K562 cells, a human erythroleukemia cell line. Induction of HLA antigens in K562 cells has been shown to make these tumor cells susceptible to both humoral and cellular immune recognition (R. T. Maziarz et al., Cell Immunol. 130:329–338, 1990).

Figure 2B:
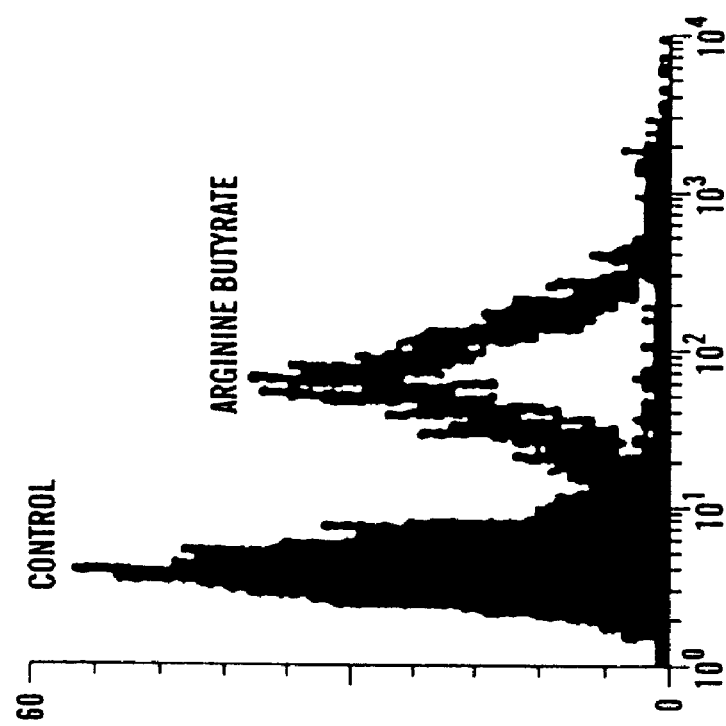
FIG. 2 Induction of expression of HLA in K562 cells (a) without and (b) with arginine butyrate.
Figure 2A:
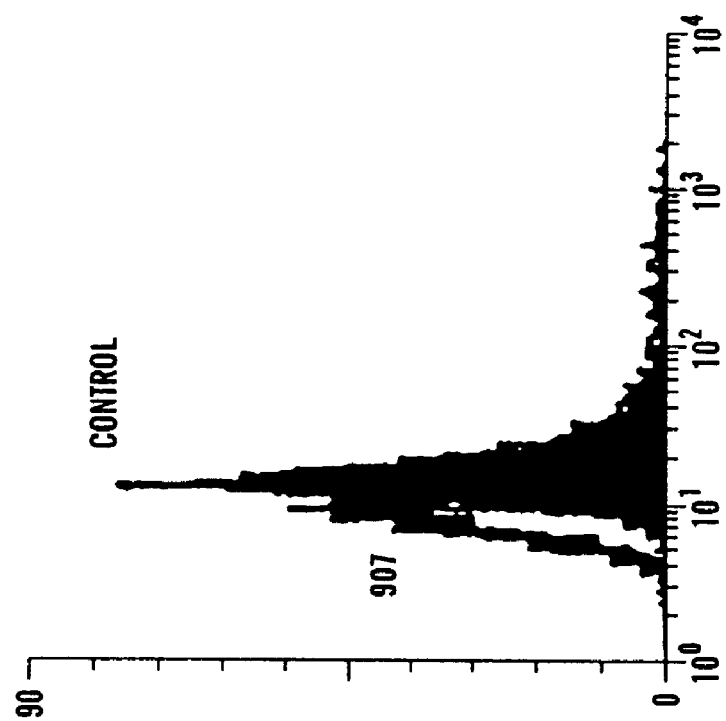

FIG. 2 shows a fluorescent activated cell sorter (FACS) analysis of HLA expression on K562 cells, before (FIG. 2a) and after one hour of exposure to 1 mM arginine butyrate (FIG. 2b) measured as described in Maziarz (Cell. Immunol. 130:329–38, 1990). HLA was increased more than 20 fold.

The IL-2 receptor is a target for therapies currently under development. For example, antibodies directed to the IL-2 receptor and conjugated to a toxin, are currently being tested in the clinic, and IL-2, itself conjugated to a toxin, is currently being tested in the clinic. Arginine butyrate has been shown to increase expression of the IL-2 receptor. This increased expression might potentiate the therapies under development.

Cytotoxic activity of arginine butyrate as a single agent and in combination with chemotherapy on cell lines with acquired drug resistance. Attempts at biomodulation of current cytotoxic chemotherapeutic agents have been described both in vitro and clinically. Agents used, such as leucovorin to increase the activity of 5-fluorouracil for colon, breast and head and neck cancer, 13-cis-retinoic acid to enhance the cytotoxicity of interferon alpha in squamous cell carcinomas of the head, neck and cervix, and calcium channel blockers to augment cytotoxicity of adriamycin in myeloma and renal cell cancer have resulted in increased tumor response rates. The mechanisms of action of these biomodulating agents include overcoming acquired/intrinsic drug resistance, cellular differentiation, and prolongation of cytotoxic drug availability. Arginine Butyrate, as a single agent, has demonstrated a marked absence of major toxicities to organ function such as the hemopoietic, hepatic, renal, pulmonary, cardiac and neurologic systems in animals and humans, which would make this an ideal compound to combine with cytotoxic agents.

Arginine butyrate was tested for cytotoxic activity alone and in combination with chemotherapeutic agents that are associated with acquired drug resistance.

When various human malignant cell lines from breast, colon, lung, prostate, ovarian and lymphoid sources were exposed to arginine butyrate cytotoxic, i.e. cell death was at 72 hours was seen at all concentrations tested between 0.1–5.0 mM.

In clinical trails with arginine butyrate, the range of serum concentrations that have been attained were between 0.05 to 1.0 mM. Combinations of arginine butyrate and chemotherapeutic agents were examined at the lower arginine butyrate concentrations.

As shown in Tables 3 and 4, the combination of arginine butyrate and cisplatin or adriamycin resulted in significant enhancement of cytotoxicity to various human tumor cell lines above that seem by each compound alone.

TABLE 3

Survival Fraction After 72 hours Exposure: AB and/or CP

| Tumor Line | Ctl | 0.5 AB | 1 CP | 2 CP | 0.5 AB/1 CP | 0.5 AB/2 CP |
|---|---|---|---|---|---|---|
| PC-3 | 1.0 | 0.67* | 0.92 | 0.49* | 0.39** | 0.26** |
| A549 | 1.0 | 0.92 | 0.77* | 0.54* | 0.33** | 0.15** |
| OvCar | 1.0 | 0.86** | 0.91 | 0.45* | 0.53** | 0.35** |

| | Ctl | 1.0 AB | 1 CP | 2 CP | 1.0 AB/1 CP | 1.0 AB/2 CP |
|---|---|---|---|---|---|---|
| CaCo | 1.0 | 0.60* | 0.87* | 0.53* | 0.22** | 0.15** |

TABLE 4

Survival Fraction After 72 Hour Exposure: AB and/or A

| Tumor Line | Ctl | 0.5 AB | .05 AB | 0.1 A | 0.5 A | 0.5 AB/0.1 A | 0.5 AB/0.5 A |
|---|---|---|---|---|---|---|---|
| A549 | 1.0 | 0.76* | 0.71* | 0.59* | 0.59* | 0.50 | 0.53 |
| PC-3 | 1.0 | 0.74* | 0.82* | 0.72* | 0.68* | 0.48** | 0.56** |
| MCF-7 | 1.0 | 0.74* | 0.89* | 0.73* | 0.69* | 0.61** | 0.63 |
| CaCo | 1.0 | 0.67* | 0.81* | 0.68* | 0.62* | 0.44** | 0.55** |
| SW900 | 1.0 | 0.92 | 0.95 | 0.82* | 0.76* | 0.61** | 0.67** |
| OvCar | 1.0 | 0.88* | 0.96 | 0.83* | 0.81* | 0.66** | 0.83 |

*Statistically significant vs. control ($p < 0.05$).
**Statistically significant vs. 1 CP, 2 CP, 0.1 A or 0.5 A as appropriate ($p < 0.05$).

Growth inhibition was measured by the MTT assay. Survival fraction is calculated from at least 3 experiments, and differences in survival fraction are statistically significant $P<0.05$, using the Paired Two-Sample For Means T-Test. Ctl=control; 0.5 AB=0.5 mM Arginine Butyrate; 1.0 AB=1.0 mM Arginine Butyrate; 1 CP=1.0. µg/ml cisplatin; 2 CP-2.0 µg/ml cisplatin; 0.05 A=0.05 µg/ml adriamycin; 0.1 A=0.1 µg/ml adriamycin; 0.5 A=0.5 µg/ml adriamycin. PC-3=prostate cancer; A549=non-small cell cancer; OvCar=ovarian cancer; CaCo=colon cancer; MCF-7=breast cancer; and SW900=non-small cell lung cancer.

These results show that Arginine Butyrate increases the cytotoxic activity of cisplatin in tumor cell lines from the lung, prostate, ovary and colon, and to a lesser extent, of adriamycin, upon human tumor cell lines from the lung, prostate, ovary, breast and colon. Other chemotherapeutic agents with non-overlapping mechanisms of antiproliferative activity such as 5-fluorouracil, taxol and interferon alpha have been evaluated with arginine butyrate. There was enhancement of cytotoxicity observed only at high concentrations of taxol exceeding 10 mM for breast and colon lines, but not in any other combination.

Figure 3:
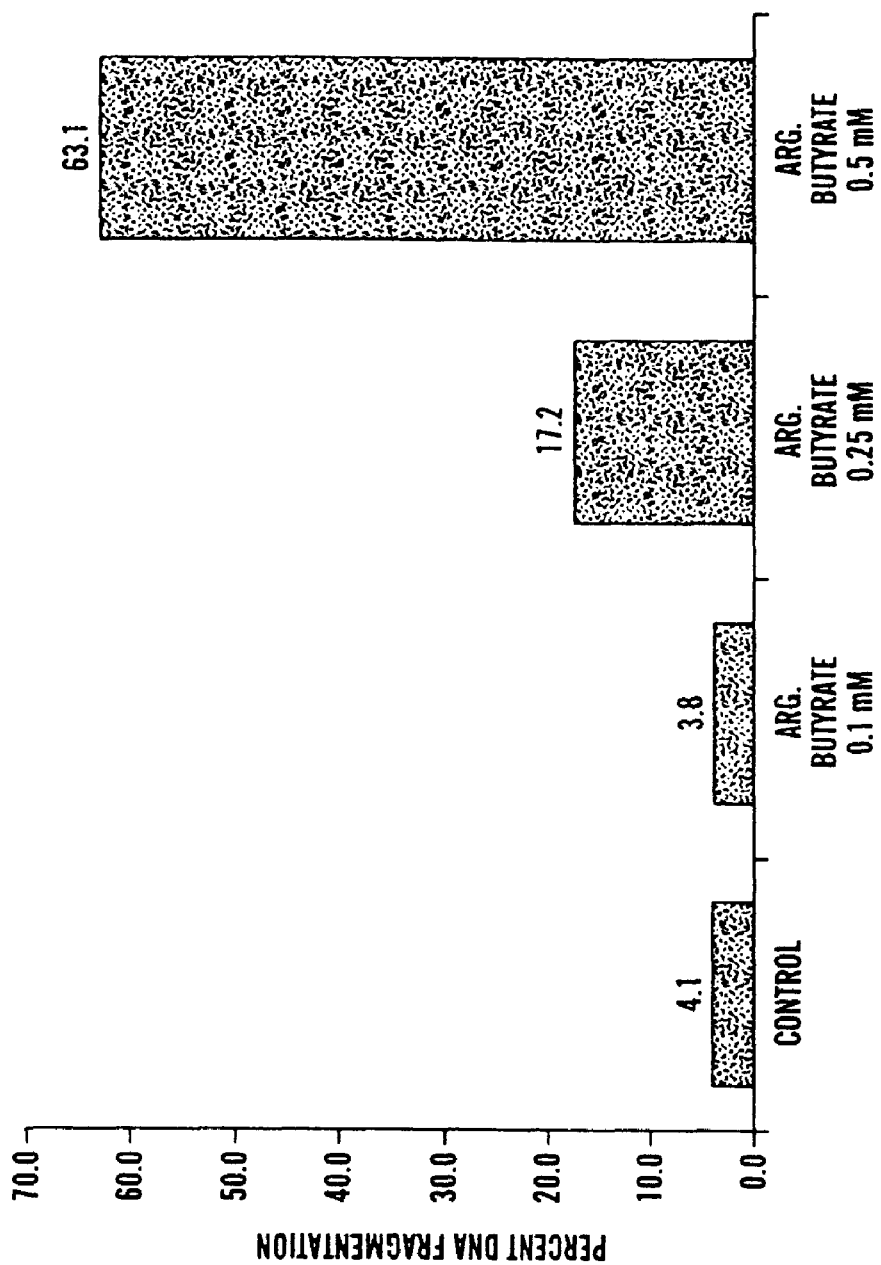
FIG. 3 Induction of DNA fragmentation with increasing amounts of arginine butyrate in K562 cells.
Figure 4:
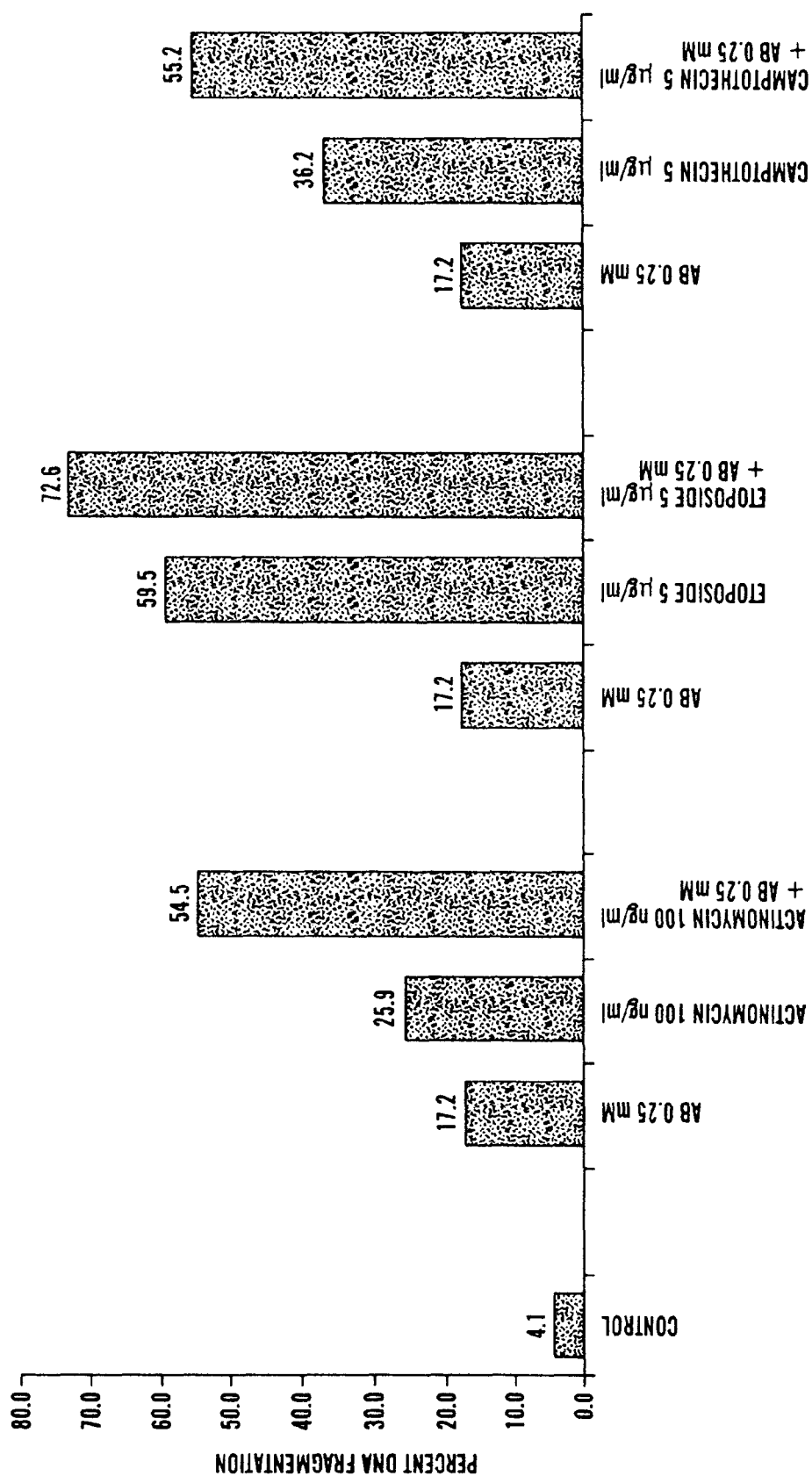
FIG. 4 Induction of DNA fragmentation with increasing amounts of arginine butyrate and with and without chemotherapeutic agents in K562 cells.
Figure 5:
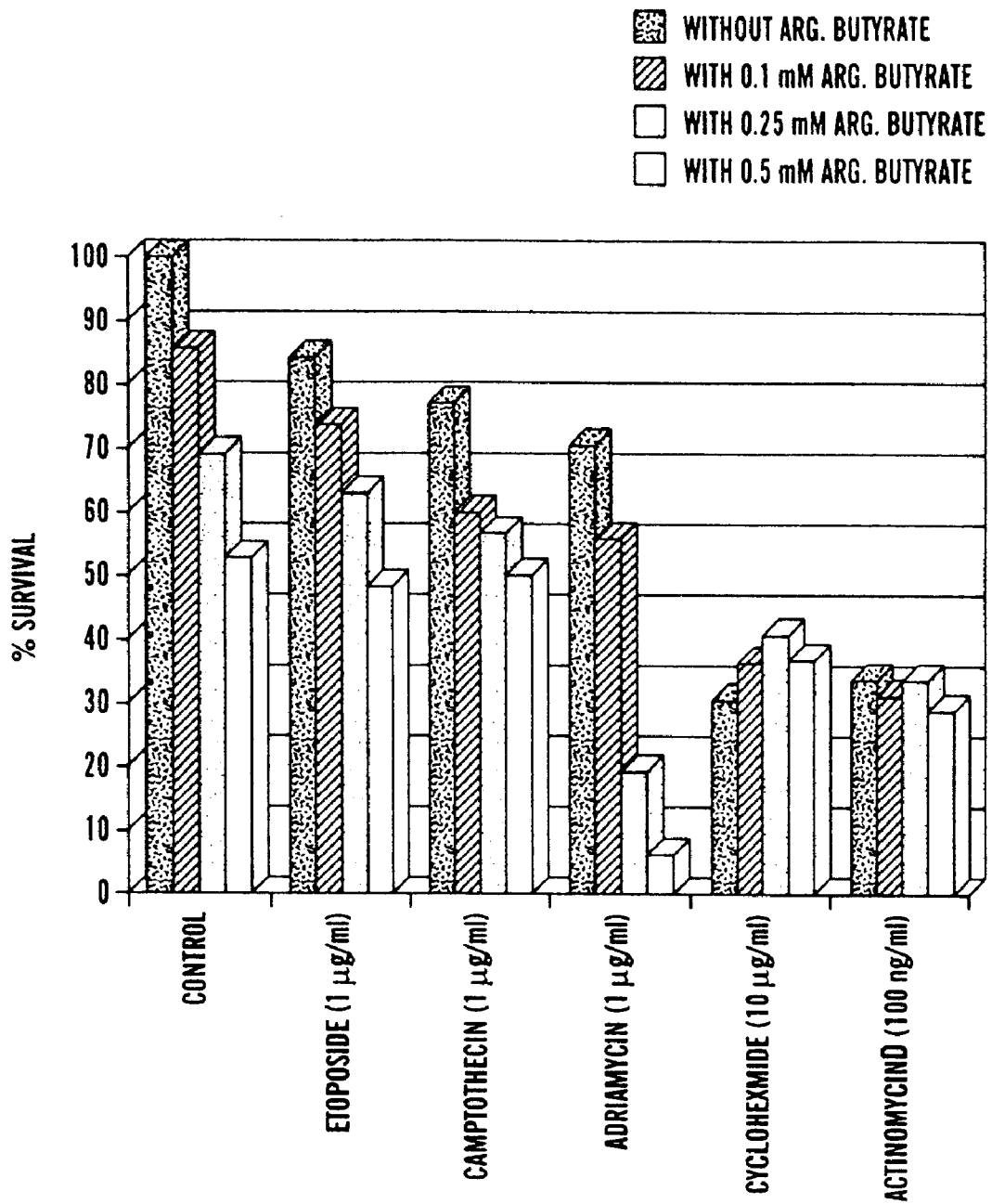
FIG. 5 Anti-proliferative effect of arginine butyrate on K562 cells in combination with chemotherapeutic agents.

Since arginine butyrate enhanced the cytotoxicity of both cisplatin and adriamycin. in drug resistance human tumor cell line, a generalized mechanism of action may explain these observations. It has been shown that sodium butyrate can induce apoptosis in human tumors or tumor cell lines (L. A. Noorduyn et al., Histopathology 21:59, 1992). In vitro evidence for DNA fragmentation and cellular shrinkage of leukemia cell lines induced by arginine butyrate supports these observations. This was observed by flow cytometry after exposure of K562 to arginine butyrate alone (FIG. 3), or in combination with other chemotherapeutic agents (FIGS. 4 and 5). DNA fragmentation was measured as described in Ginis and Faller (Anal. Biochem. 219:288–96, 1994) and survival was measured by the MTT assay. As shown in these figures, the addition of arginine butyrate increased their apoptotic activity to all of the following compounds: etoposide, camptothecin, adriamycin, cyclohexamide, and actinomycin D. Lack of enhancement with cyclophosphamide and actinomycin D was perhaps due to maximal DNA fragmentation by these two compounds alone at the concentrations selected.

Although it has been shown that both cisplatin and adriamycin can induce apoptosis, evidence for DNA fragmentation or cellular shrinkage by flow cytometry was not observed after exposure to arginine butyrate alone, or in combination with cisplatin or adriamycin in tumor cell lines A549, PC-3 and CaCo. These results suggest that at the lower concentration of arginine butyrate (0.1–0.5 mM), apoptosis is not the mechanisms of action for enhanced cytotoxicity observed when combined with cisplatin or adriamycin in these cell lines.

Figure 6:
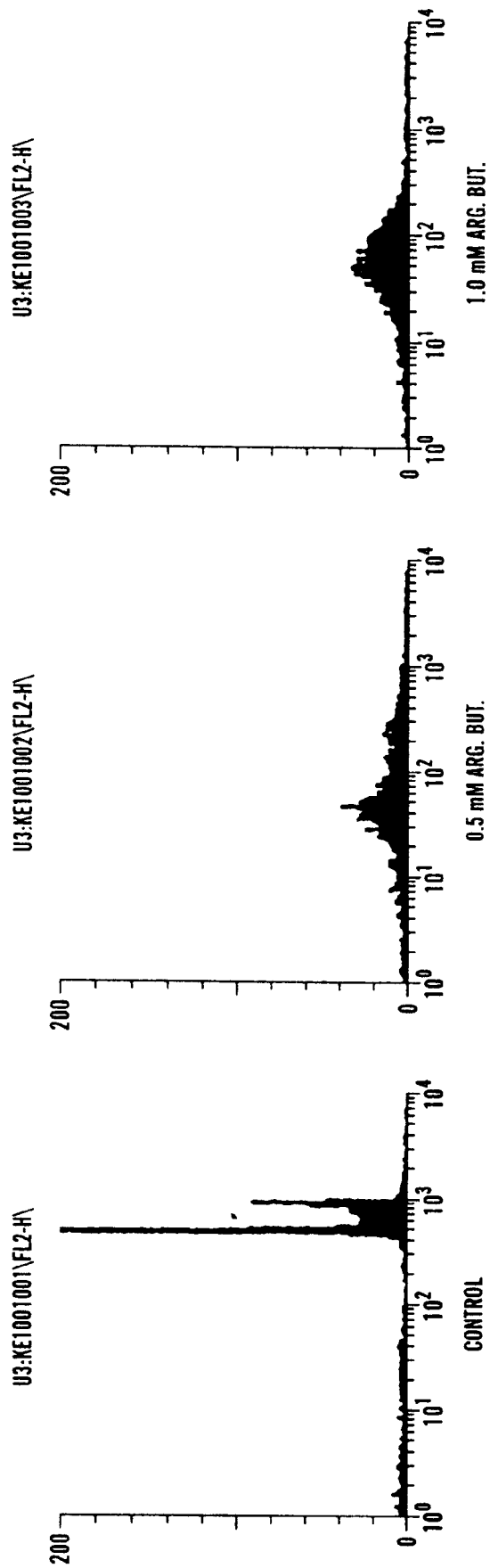
FIG. 6 Induction of apoptosis by (a) 0 mM, (b) 0.5 mM, and (c) 1.0 mM arginine butyrate in the SY5Y neuroblastoma cell line.

However, when induction of apoptosis by arginine butyrate in the human neuroblastoma cell line, SY5Y, was measured, significant DNA fragmentation was found with both 0.5 and 1.0 mM concentrations (FIGS. 6a–c).

Example 10 Cytotoxic Activity of Arginine Butyrate and Ganciclovir on EBV+Tumor Cells.

Neoplastic Cells Epstein-Barr virus (EBV) is a 172 kb herpesvirus. Virus tropism is determined by complement receptor type 2 which mediates attachment of the envelope protein gp350/250 to B and some T lymphocytes, follicular dendritic cells and epithelial cells. In vivo EBV undergoes lytic replication after initial infection of oropharyngeal epithelia. The genome in linear form is duplicated, packaged into the viral capsid and extruded from the cell by budding or lysis. One hundred viral proteins are synthesized during this lytic stage of the virus life cycle.

In contrast, normal B-cells incubated with EBV in vitro are efficiently immortalized and develop into continuously growing lymphoblastoid cell lines (LCLs). The cellular events regulating these distinct outcomes are not understood. In immortalized cells, the genome circularizes, amplifies and replicates coordinate with, and dependent upon, cell division. Because no viral particles are produced, infection is considered to be latent. EBV persists in B-cells for life. Outgrowth of latently infected B-cells is prevented by T-cell immune surveillance. In immortalizing latent infection, only 11 gene products are detected, including 6 nuclear antigens (EBNA-1, -2, -LP, -3A, -3B, -3C), 3 membrane proteins (LMP-1, LMP-2A, LMP-2B) and two small, non-poly (A) RNAs (EBER-1, EBER-2). In EBV+ tumors such as Burkitt's lymphoma, neoplastic genetic events have often superseded the requirements for viral immortalizing functions, and gene expression may be limited to EBNA-I.

EBV is a common and worldwide pathogen. Childhood infection is asymptomatic. Fifty percent of individuals with delayed exposure develop a self-limited lymphoproliferative syndrome, infectious mononucleosis. EBV is also detected in 2 endemic tumors: African Burkitt's lymphoma (BL) and nasopharyngeal carcinoma (NPC). Recently, some T-cell and B-cell lymphomas, as well as 50% of Hodgkin's lymphomas have been found to contain EBV.

The development of a large patient population with T-cell dysfunction in the 1980's, caused by profound iatrogenic immunosuppression required to facilitate solid organ and bone marrow transplantation and by the AIDS epidemic, led to the discovery of two additional EBV-related illnesses; hairy leukoplakia, and B-lymphoproliferative disease (EBV-LPD).

In cells productively infected with EBV, EBV thymidine kinase (TK) is expressed. This makes these cells susceptible to treatment with ganciclovir (GCV). GCV is phosphorylated by EBV-TK and the resulting accumulation of phosphorylated GCV inhibits synthesis of DNA, which in turn leads to cell death. In vivo efficacy of GCV was established in hairy leukoplakia, a lytic EBV disease, wherein the production of virus leads to cell lysis. However, most EBV+ neoplasms are not lytic, rather they are latent infections. In the absence of viral production, TK is either not produced or produced at low levels and therapy with GCV is therefore, not an effective treatment.

Figure 7:
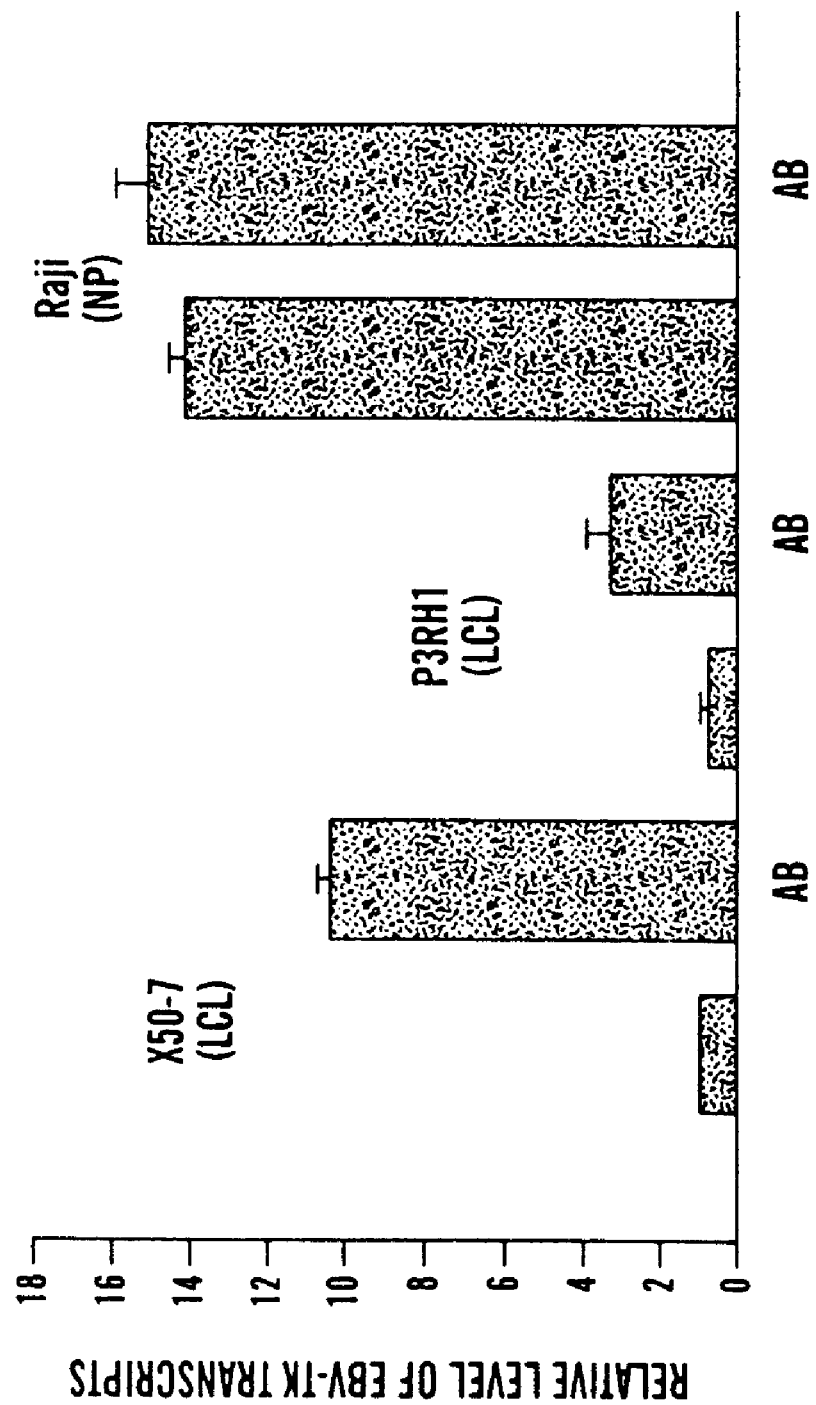
FIG. 7 EBV-TK gene induction by arginine butyrate.

Because of arginine butyrate's ability to induce various genes, its ability to induce EBV-TK mRNA in human lymphoma cell lines was evaluated. FIG. 7 provides bar graphs of the basal levels of TK and the levels following 12 hours of incubation with 3 mM arginine butyrate in 3 lymphoma cell lines: X50–7 a latent large cell lymphoma (B cell); P3RH1 an EBV B-cell producer line derived from Burkitt's lymphoma; and Raji a non-producer line derived from a Burkitt's lymphoma. EBV-TK levels were not increased in the EBV non-producer cell line, Raji, which has a high basal level of TK, but were increased approximately 4 fold in an EBV producer cell line and 10 fold in a non-producer cell line.

Figure 8A:
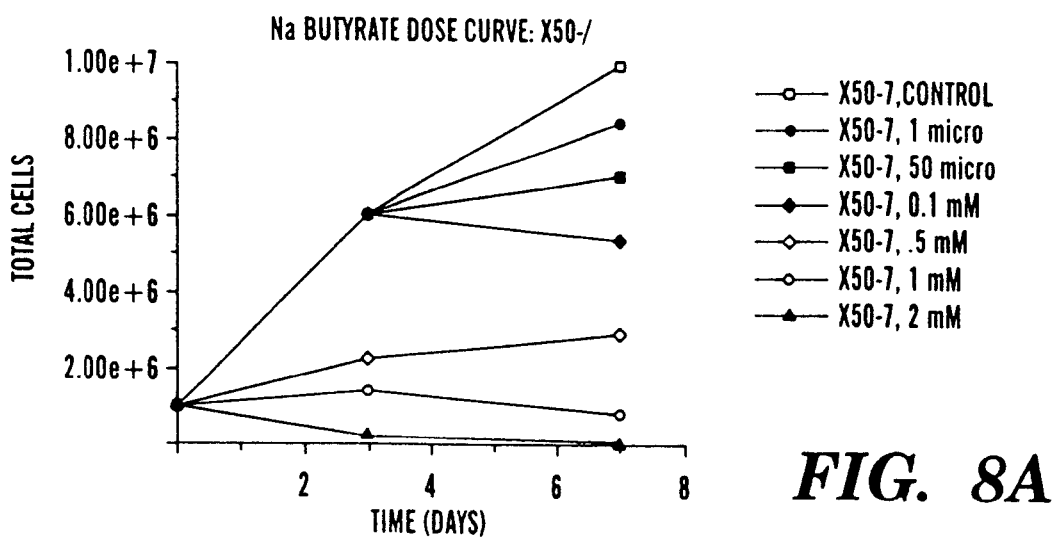
FIG. 8 Growth curves of EBV+ and EBV− cell lines in butyrate: (a) four cell lines in 2 mM butyrate; (b) X50–7 in different concentrations of butyrate; and (c) HPB-ALL in different concentrations of butyrate.
Figure 8B:
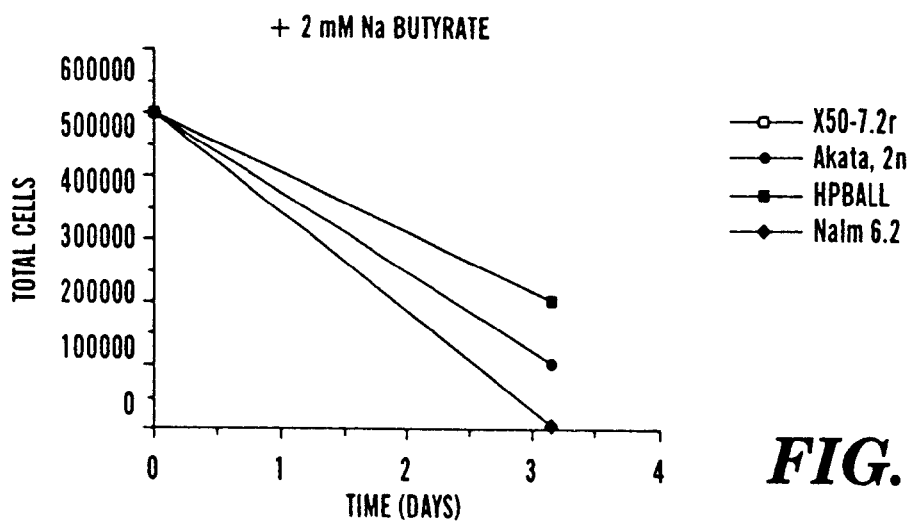
Figure 8C:
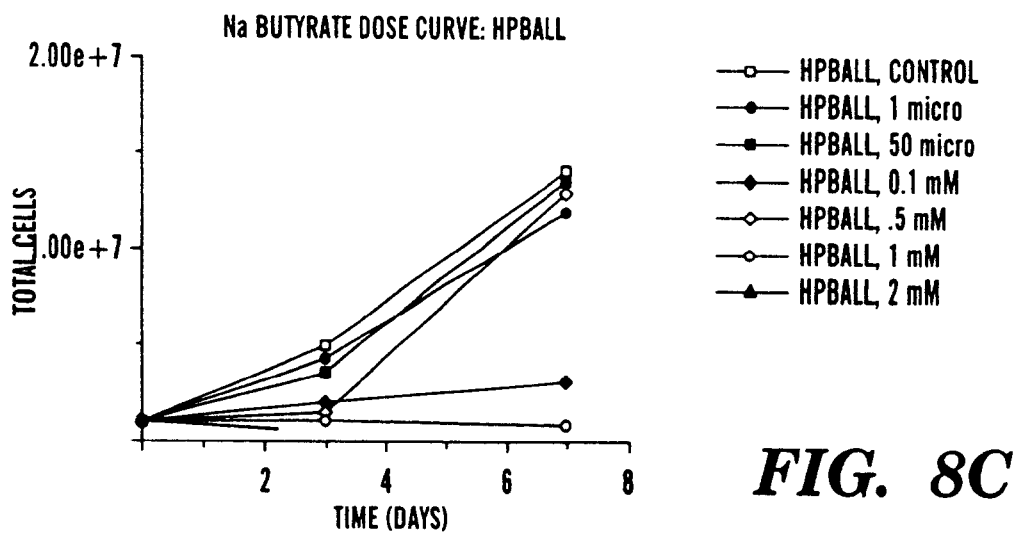
Figure 9A:
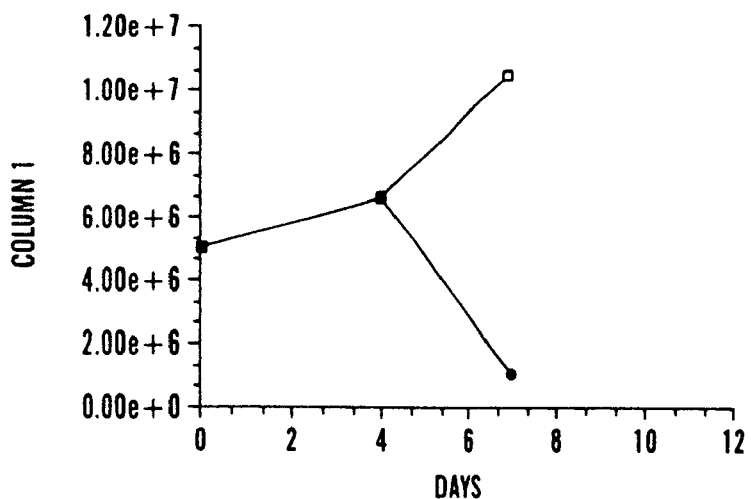
FIG. 9 Inhibition of growth of EBV+tumor lines by (a) 0.5 mM and (b) 2.0 mM arginine butyrate and GCV.
Figure 9B:
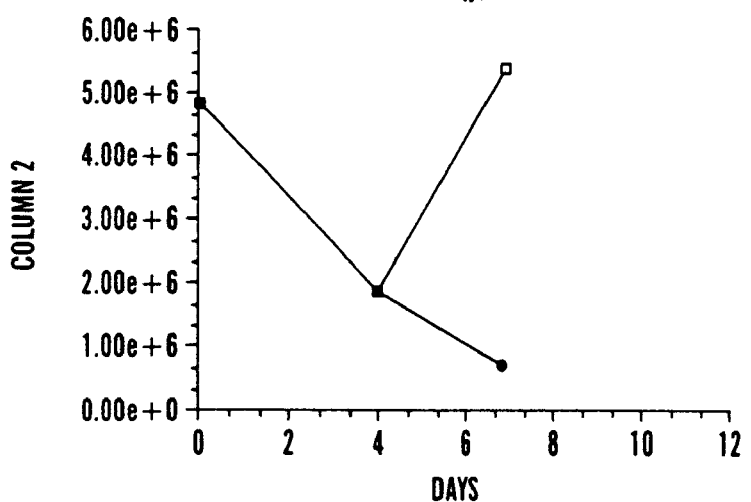

In some experiments sodium was used instead of arginine to neutralize butyric acid. In dose response experiments, levels of EBV-TK MRNA plateaus at around 1 mM to 3 mM sodium butyrate, inducing levels essentially equivalent to those induced by 1 mM arginine butyrate. However, arginine butyrate at 2 mM and 3 mM was cytocidal to most EBV+ and EBV− cell lines while 1 mM was cytostatic to some cell lines and permitted normal cell growth in others. Similarly, levels of GCV above 30 $\mu$M were generally cytocidal to both to EBV+ and EBV− cell lines. Cell lines used were X50–7, a latent EBV+ B-cell lymphoma; Akata, a producer EBV+ Burkitt's lymphoma; HPB-ALL, a T-cell line; and Nalm-6, an EBV− B-cell line. Growth curves of all four cell lines in 2.0 mM sodium butyrate are shown in FIG. 8a. Growth curves for X50–7 cells in different concentrations of sodium butyrate are shown in FIG. 8b and the growth curves for HPB-ALL cells in different concentrations of sodium butyrate are shown in FIG. 8c.

Levels at or below 1 mM arginine butyrate and 30 $\mu$M GCV were chosen to study in combination with each other for ability to kill EBV+ tumor cells. FIGS. 9–14 demonstrate the growth inhibition and cytotoxic effect of these agents used in combination at these doses, but not when used alone, on both EBV+ lymphoma lines (FIGS. 9a and 9b) and a fresh tumor isolate (FIGS. 13 and 14) of a patient concurrently treated with arginine butyrate and GCV.

Figure 10:
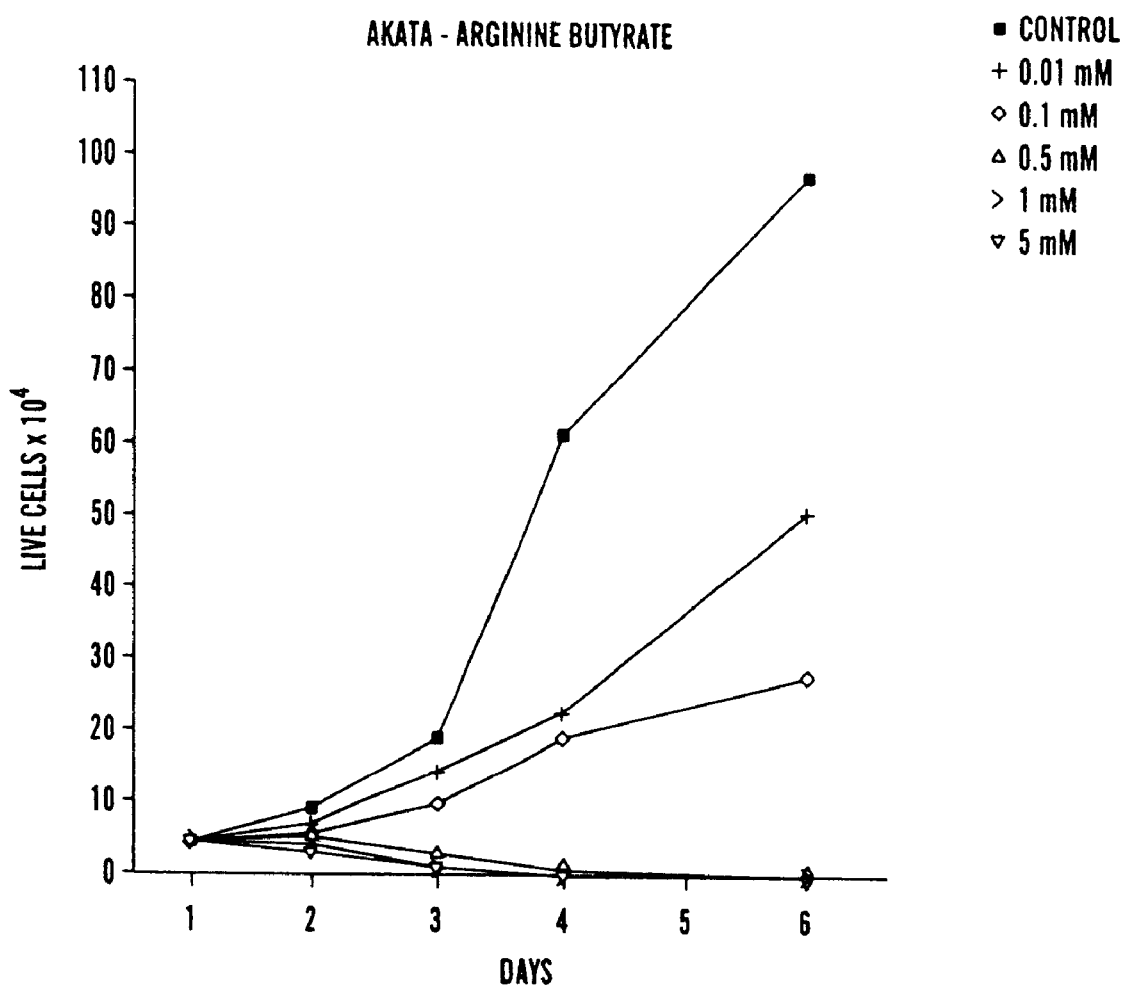
FIG. 10 Growth curve of the Akata cell line in different doses of arginine butyrate.
Figure 11:
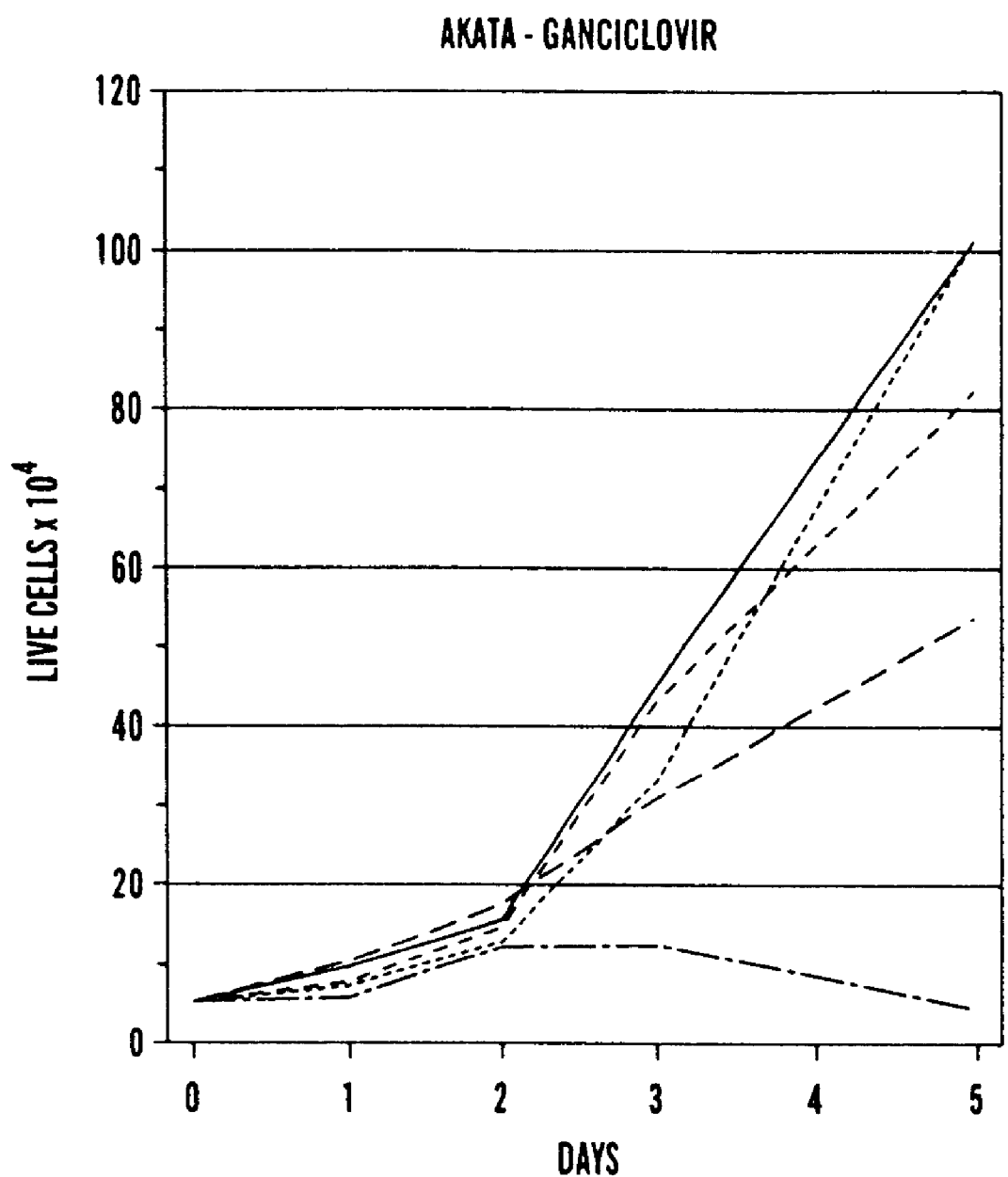
FIG. 11 Growth curve of the Akata cell line in the presence of GCV.
Figure 12:
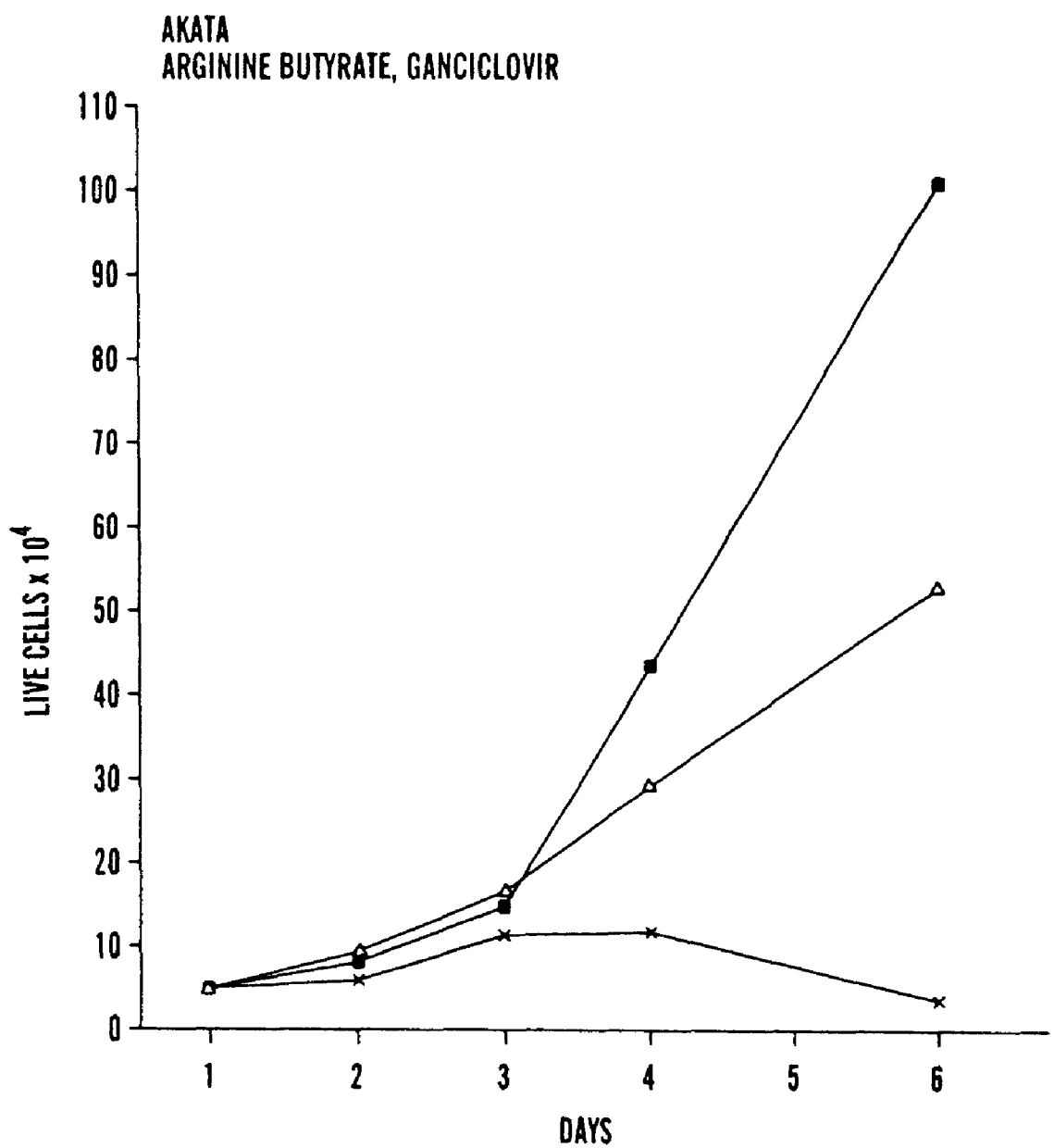
FIG. 12 Comparison of the growth curves of the Akata cell line in the presence of arginine butyrate, GCV and both arginine butyrate and GCV.

JY is an EBV+ B-cell LCL that is latent. The JY cells were incubated in the presence of 0.5 mM (non-toxic) (FIG. 9a), or 2.0 mM (non-toxic) arginine butyrate (FIG. 9b) for 3 days, after which time Arginine Butyrate was washed out and GCV added to some plates (+) at 0.5 $\mu$M. Because of TK induction, JY cells were killed efficiently at the non-toxic doses of the individual drugs. EBV cells coincubated with arginine butyrate and then GCV at non-toxic doses were unaffected. Growth curves for the Akata cell line (a latent EBV+ cell LCL), grown in different concentrations of arginine butyrate are shown in FIG. 10. Growth curves for the Akata cell line grown in the presence of different concentrations of GCV are shown in FIG. 11. These cells were then cultivated in the presence or absence of non-toxic doses of arginine butyrate at 1.0 mM, 0.5 $\mu$M GCV or the combination of both arginine butyrate and GCV. Growth curves for the combination are shown in FIG. 12. As can be seen, the combination was clearly much more toxic, and effective, that either agent alone.

There have been reports that butyrate induces activation/transcription from the HIV-1 promoter in transient-expression assays(C. A. Bohan et al., Virol. 172:573–83, 1989; C. A. Bohan et al., Biochem. Biophys. Res. Comm. 148:899–905, 1987; A. Yeivin et al., Gene 116:159–64, 1992; D. -C. Tang et al., Biochem. Biophys. Res. Comm. 169:141–47, 1992), and also that butyrate causes death of HIV-1 infected cells (M. R. Sadaie et al., Virol. 202:513–18, 1994). In addition, a recent report demonstrated that butyrate, in Kaposi's sarcoma-associated herpes virus patients, enhances Herpes virus type 6 gene expression (G. Miller et al., N. Engl. J. Med. 334:1292–98, 1996).

Figure 13:
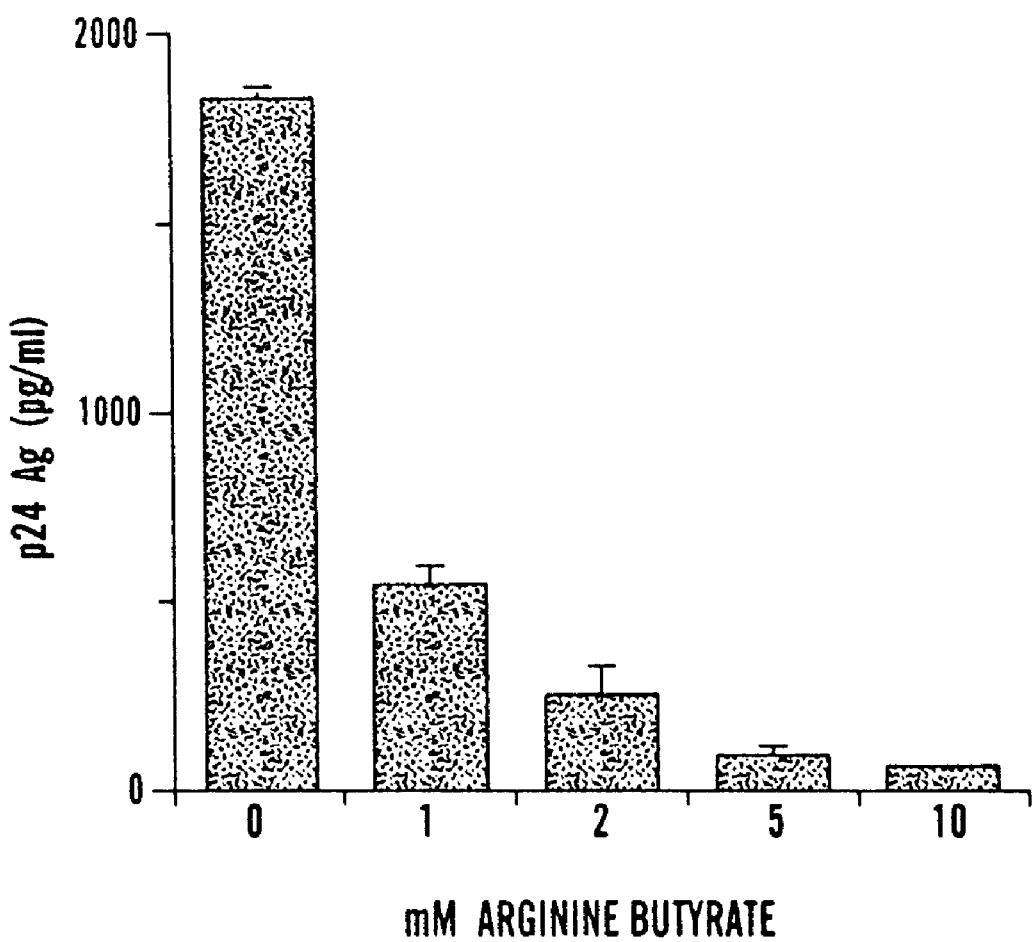
FIG. 13 HIV p24 levels, assayed by radio-immuno assay, in PBMCs and Ci11s isolated 72 hours post-cultivation in arginine butyrate.

The effect of arginine butyrate on HIV p24 production could be easily studied in co-cultures of human PBMC and Ci11, an HIV infected cell line. As shown in FIG. 13, the addition of arginine butyrate led to a significant decrease in p24 production. Despite these encouraging results with a more direct assay than those published previously, the potential risks to HIV+ patients of treatment with arginine butyrate have not been evaluated as these patients were excluded from the protocol (FIG. 13). HIV p24 levels assessed by radio-immuno assay.

In summary, arginine butyrate has multiple properties each of which could presage success as an anti-cancer treatment. Arginine butyrate induces terminal differentiation in developmentally arrested human tumor cell lines. These now terminally mature cells are subject to the normal, restricted cell growth characteristic of fully differentiated cells and no longer proliferate in the uncontrolled fashion characteristic of malignant neoplastic cells.

Arginine butyrate induces cellular proteins which render the cell susceptible to immunotherapy or directed cytotoxicity. For example, one reason neoplastic cells escape immune surveillance is lack, of or under-expression of, HLA antigens. Arginine butyrate induces expression of HLA antigens on human tumor cells, making them susceptible to humoral and cellular immune recognition. Arginine butyrate also induces the expression of IL-2 receptors making them susceptible to directed cytotoxic therapy.

Arginine butyrate is directly cytotoxic to drug resistant cell lines. The addition of cisplatin or adriamycin produces a statistically significant increase in cytotoxic in the cell lines which are resistance to cisplatin or adriamycin alone.

Finally, arginine butyrate induces EBV-TK MRNA and combination treatment with arginine butyrate and GCV is cytotoxic to EBV+ lymphoma cell lines and fresh isolates of EBV+ lymphoma cells at serum levels achievable in humans.

Example 11 Previous Human Experience.

Human experience with butyrate involves more than 25 patients with β-hemoglobinopathies, 9 patients in a traditional end-stage cancer patients and three compassionate patients with EBV+ lymphomas. Children with acute myelogenous leukemia and children with neuroblastoma have been treated with sodium butyrate. Doses of sodium butyrate ranging from 0.5–1.5 g/kg/day for 14 days, and 10 g/kg/day IV infusions were given without toxic side effects.

Eleven pediatric and twelve adult patients with β-hemoglobinopathies have been treated with IV arginine butyrate at a starting dose of 500 mg/kg/day for 2–7 weeks. Dose escalation at the rate of 250 mg/kg/day to a maximum of 2,000 mg/kg/day was permitted. There were no grade 3 or 4 toxicities and most patients showed response as judged by increase in fetal globin mRNA.

An inter-group dose-escalation study is being conducted in patients with refractory malignancies. There are 3 patients per group with the dose levels starting at 500 mg/kg/day, and increasing by 250 mg/kg/day per group, if toxicity permits. Doses are given by 8 hour IV infusion, daily, for 5 days times 2 weeks, with weekends off, for a total of 10 days of treatment per cycle.

In the first dose group, three patients with refractory neoplasms (breast, melanoma, adenocarcinoma of unknown primary) were enrolled and completed 1–2 cycles of arginine butyrate at a dose of 500 mg/kg/day given over 6–8 hours, by IV infusion, for 10 days over a 2 week period (F. M. Foss et al., Proc. ASCO 13:162, 1994; D. A. Sanders et al., Proc. ASCO, 1995; F. M. Foss et al., Proc. ASCO 13:162, 1995). There were no objective toxicities noted for the hepatic, renal, cardiac, pulmonary or hematopoietic systems. Two of the three patients experienced grade I nausea/vomiting which was controlled with oral anti-emetics. No objective tumor responses were noted.

In the second dose group, three patients (breast cancer, bowel cancer, Hodgkin's disease) have completed 2 cycles of arginine butyrate at a dose of 750 mg/kg/day for 10 days. One, of the three patients had grade I nausea/vomiting which was controlled with oral anti-emetics. One patient had a transient elevation of serum BUN, without elevation of serum Cr, and proteinuria measured by dipstick. These abnormalities resolved within 5 days of discontinuation of the drug. Otherwise, there were no other objective signs of organ toxicity. Two patients had stable disease after two cycles, with no progression. Tumors progressed after treatment was stopped. The patient with Hodgkin's disease had a partial response (>80%) reduction in tumor area) after the first cycle, with resolution of lymphadenopathy and leukocytosis, and complete resolution of back pain, with all narcotics stopped. He had further resolution of disease during the second cycle. Disease progression was noted one month after the second cycle was completed.

In the third dose group, three patients have been enrolled on study and are being treated at 1,000 mg/kg/day.

Figure 14:
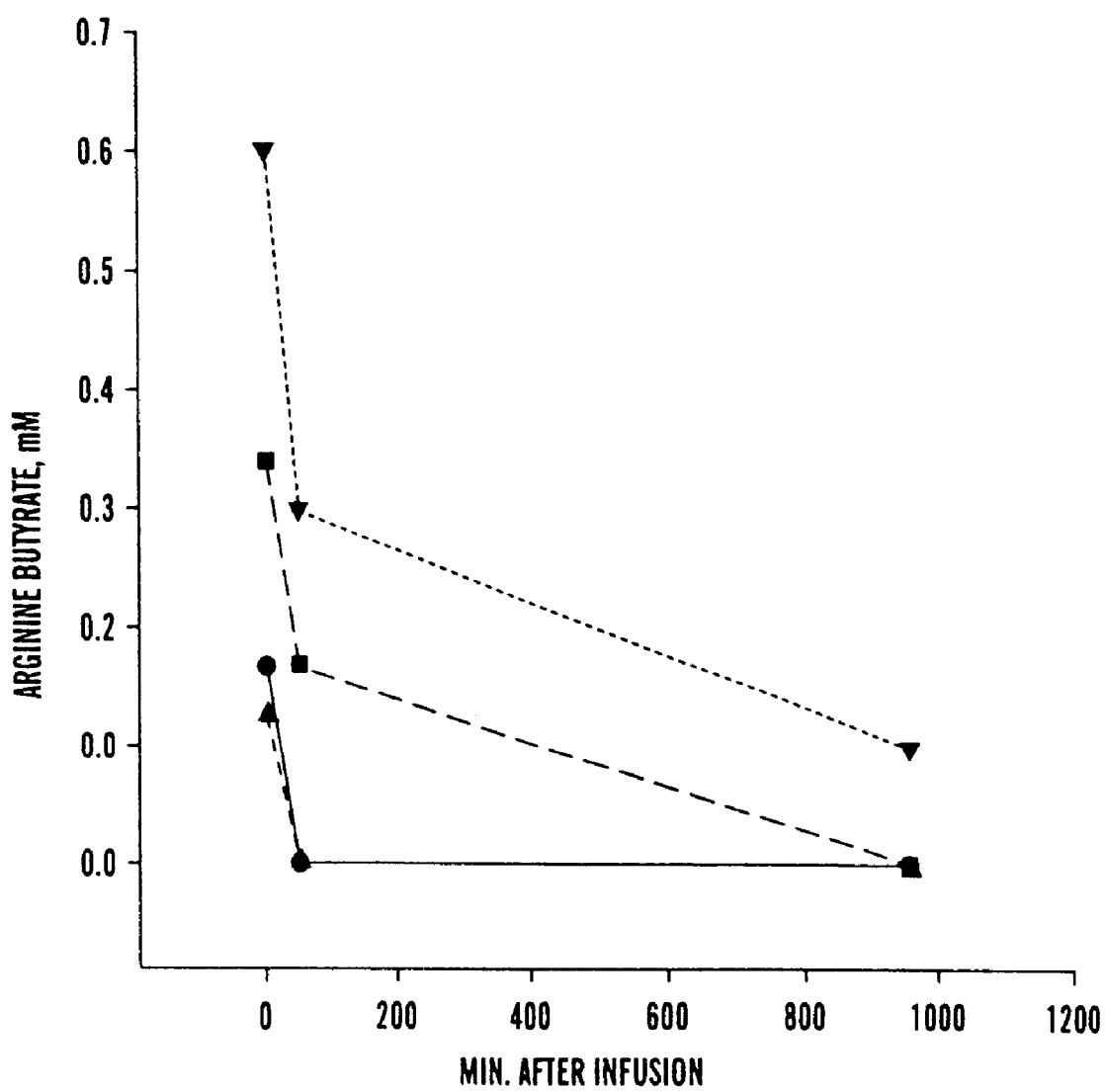
FIG. 14 Pharmakinetics of arginine butyrate infusion.

The pharmacokinetics in the cancer patients show dose response and are similar to the pharmacokinetics reported patients with β-hemoglobinopathies. FIG. 14 shows a plot of the serum levels following the first dose for four patients in the oncology study.

Three cancer patients were treated on an emergency basis. Because of their significantly advanced condition they were treated up to 2,000 mg/kg/day by 12–24 hours. IV infusion, daily for 10 days, a dose felt to be safe and therapeutic. There were no untoward side effects noted in any of these patients.

Finally, two patients with post-transplant EBV-induced lymphomas have been treated on a compassionate basis with IRB approval. Each patient is summarized below.

Patient one was a 38 year old male, 2 months post lung transplant. He was receiving cyclosporin to prevent impending rejection. He developed massive lymphadenopathy in mediastinum and hilum, with progressive respiratory failure.

He was biopsy positive for EBV, and the tumor cells were monoclonal and of donor origin.

Figure 15:
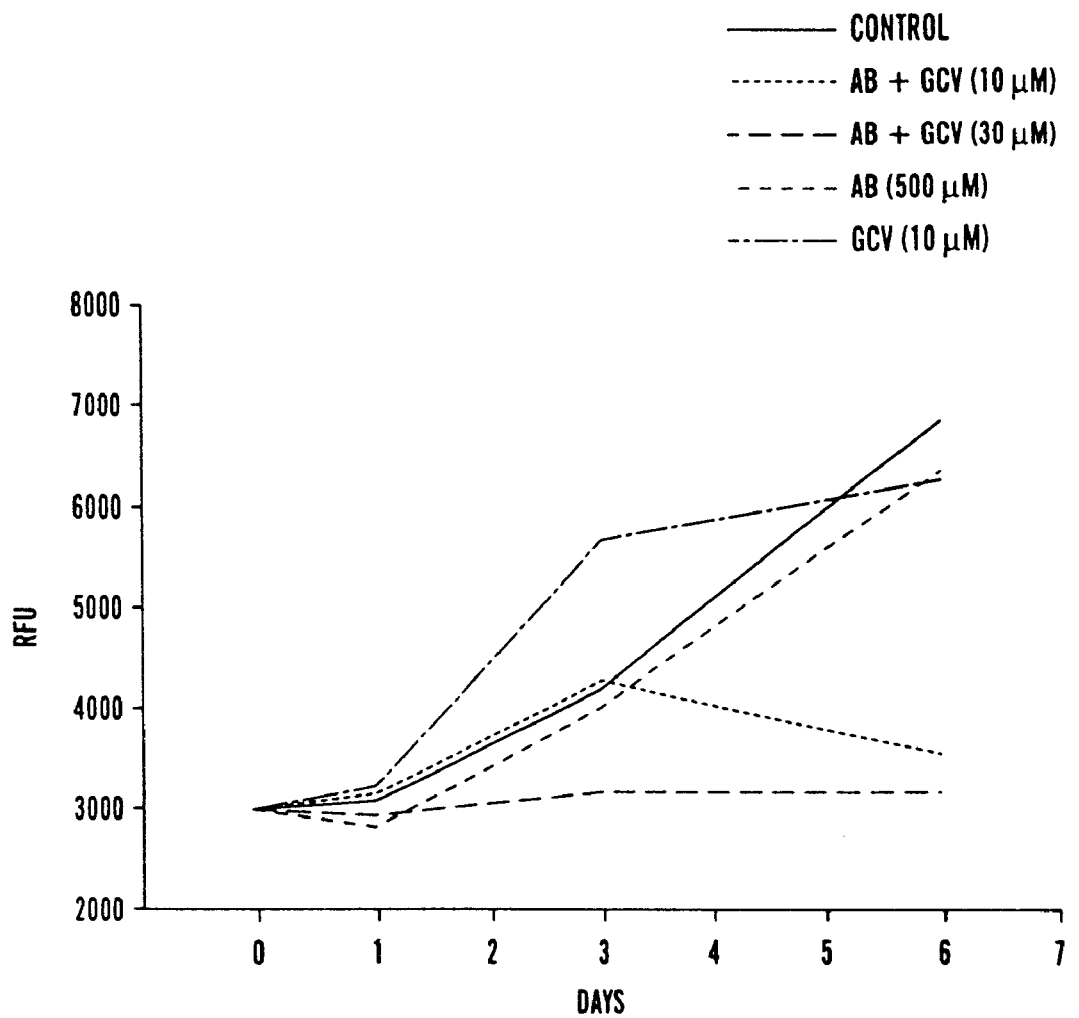
FIG. 15 Inhibition of EBV+ tumor cell proliferation in cells freshly isolated from a patient with LPD.
Figure 16:
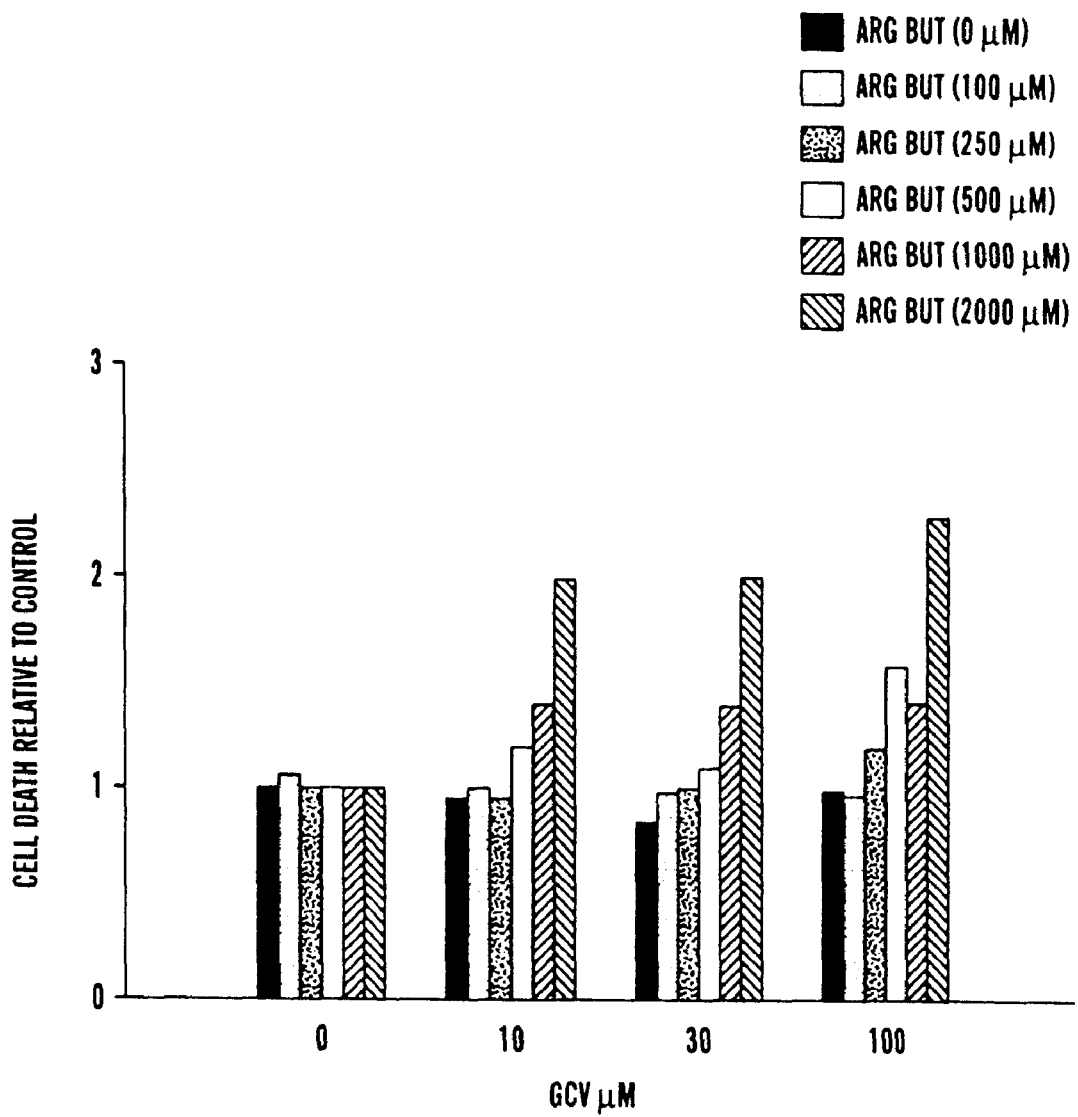
FIG. 16 Prior cell death with combination therapy on day 3 in cells freshly isolated from a patient with LPD.

This patient's circulating tumor cells grew in culture and, since initiation of clinical treatment was urgent, were tested in vitro with arginine butyrate and GCV post start of in vivo therapy. As shown in FIGS. 15 and 16, treatment with arginine butyrate and GCV was cytotoxic to this patient's cells. The patient had been previously treated with and had no response to XRT, CHOP (developed severe neutropenia and *Aspergillus* septicemia), or α-IFN plus gamma globulin. Cell death in FIG. 16 was measured by the uptake of ethidium homodimer.

He had been off all therapy, except ganciclovir, for 3 weeks when he started arginine butyrate at 1,000 mg/kg/day. He had been on GCV for 2 weeks, but showed no response. After starting arginine butyrate, he showed progressive resolution of tumor by radiography during the 21 day treatment. He eventually died from *Aspergillus* infection. At postmortem there was no evidence of lymphoma.

The second patient was a 23 year old female, 4 months post-allogeneic bone marrow transplant for leukemia. She was receiving cyclosporin to prevent rejection. She developed cervical, mediastinal and abdominal lymphadenopathy, with brain metastases. A biopsy was positive for EBV and tumor cells were monoclonal confirming the diagnosis of LPD.

She had been treated with and had no response to XRT, CHOP, or α-IFN plus gamma globulin. She had been off all therapy for 2 weeks and was cachectic, too weak to ambulate, paraplegic, in constant pain and had been admitted for terminal care, when she started arginine butyrate at 1,000 mg/kg/day and ganciclovir.

Within one day she began eating and walking. By day 14, she had experienced complete resolution of her systemic tumor and substantial resolution of CNS metastases, as documented by radiography. Her treatment continued for 21 days. Her CNS lesions are now stable by MRI. The residual findings may represent scarring, in which case this patient would be scored as a CR. She has been well and off therapy for longer than 9 months.

In total, more than 40 patients have been treated with arginine butyrate (>25 with β-hemoglobinopathies and >15 with neoplasia). Doses used were up to 2,000 mg/kg/day given over 8 to 24 hours per day, for more than 4 weeks in patients with β-hemoglobinopathies, with some of these patients having been treated for more than a year, and for up to 2 cycles of 10 days of treatment per cycle. Arginine butyrate has been well tolerated with no grade 3 and no grade 4 toxicities reported. Importantly, two patients with EBV-associated disease have been treated, not only safely, but with significant clinical improvement.

Other embodiments and uses of the invention will be apparent to those skilled in the art from consideration of the specification and practice of the invention disclosed herein. All U.S patents and other documents referenced herein, for what ever reason, are specifically incorporated by reference. It is intended that the specification and examples be considered exemplary only, with the true scope and spirit of the invention being indicated by the following claims.

I claim:

1. A method for treating a virus-induced, cell proliferative disorder comprised of administering an inducing agent and an anti-viral agent to a patient suspected of having said disorder wherein the inducing agent induces the expression of a viral gene product in proliferating cells associated with said disorder.

2. The method of claim 1 wherein the cell proliferative disorder is a neoplasia.

3. The method of claim 1 wherein the inducing agent and the anti-viral agent are administered parenterally, sublingually, rectally, enterally, by pulmonary absorption or by topical application.

4. The method of claim 1 wherein the viral gene product is expressed from a virus infecting said proliferating cells.

5. The method of claim 1 wherein the viral gene product is expressed from a latent virus selected from the group consisting of an Epstein-Barr virus (EBV), a Kaposi's-associated human herpes virus (human herpes virus 8), a human immunodeficiency virus (HIV), and a human T-cell leukemia/lymphoma virus (HTLV).

6. The method of claim 1 wherein the viral gene product is a viral protein that regulates gene expression.

7. The method of claim 1 wherein the viral gene product is a viral enzyme, an oncogene or proto-oncogene, a transcription factor, a protease, a polymerase, a reverse transcriptase or a combination thereof.

8. The method of claim 1 wherein the viral gene product expressed sensitizes the proliferating cells to the anti-viral agent.

9. The method of claim 2 wherein the neoplasia is selected from the group consisting of leukemias, lymphomas, sarcomas, carcinomas, neural cell tumors, squamous cell carcinomas, germ cell tumors, undifferentiated tumors, seminomas, melanomas, neuroblastomas, mixed cell tumors, metastatic neoplasia and neoplasia due to pathogenic infections.

10. The method of claim 2 wherein the neoplasia is a nasopharyngeal carcinoma, Hodgkin's disease, Burkitt's lymphoma, non-Hodgkin's lymphoma, hairy leukoplakia, a B cell or T cell lymphoproliferative disorder, breast cancer, gastric cancer or lung cancer.

11. The method of claim 7 wherein the viral enzyme is a thymidine kinase.

12. A method for treating a patient having a cell proliferative disorder resulting from a viral infection, wherein said virus contains a viral thymidine kinase (tk) the method comprising:
    (a) determining if said patient has cells affected by said cell proliferative disorder that are positive for viral genomes, transcripts, or antigens;
    (b) selecting patients having such virus (+) cells; and
    (c) administering an inducing agent and an anti-viral to said patient.

13. A method for treating a patient having a disorder resulting from or associated with a herpesvirus comprising:
    (a) determining if said patient has been exposed to said herpesvirus;
    (b) administering an inducing agent to said patient, who has been exposed, wherein the inducing agent induces the expression of herpesvirus gene product in cells infected from said viral infection; and
    (c) administering an anti-viral agent to said patient.

14. A method for treating a patient having a cell proliferative disorder resulting from or associated with herpesvirus comprising:
    (a) determining if said patient has been exposed to said herpesvirus ; and
    (b) administering an inducing agent and an anti-viral agent to said patient, who has been exposed.

* * * * *